US009259447B2

(12) United States Patent
Burcelin et al.

(10) Patent No.: US 9,259,447 B2
(45) Date of Patent: Feb. 16, 2016

(54) LACTIC ACID BACTERIA AND BIFIDOBACTERIA FOR TREATING ENDOTOXEMIA

(75) Inventors: Rémy Burcelin, Escalquens (FR); Didier Carcano, Paris (FR); Pierre Desreumaux, Lille (FR); Sampo Lahtinen, Siuntio (FI); Nina Rautonen, Espoo (FI); Heli Putaala, Kirkkonummi (FI); Kirsti Tiihonen, Helsinki (FI); Rodolphe Barrangou, Madison, WI (US)

(73) Assignee: DUPONT NUTRITION BIOSCIENCES APS (DK)

( * ) Notice: Subject to any disclaimer, the term of this patent is extended or adjusted under 35 U.S.C. 154(b) by 752 days.

(21) Appl. No.: 13/384,748

(22) PCT Filed: Jul. 30, 2010

(86) PCT No.: PCT/IB2010/053482
§ 371 (c)(1),
(2), (4) Date: Apr. 5, 2012

(87) PCT Pub. No.: WO2011/013106
PCT Pub. Date: Feb. 3, 2011

(65) Prior Publication Data
US 2012/0183516 A1 Jul. 19, 2012

Related U.S. Application Data

(60) Provisional application No. 61/229,980, filed on Jul. 30, 2009, provisional application No. 61/312,400, filed on Mar. 10, 2010, provisional application No. 61/321,949, filed on Apr. 8, 2010, provisional application No. 61/325,919, filed on Apr. 20, 2010.

(51) Int. Cl.
*A61K 35/74* (2015.01)
*A61K 35/745* (2015.01)

(52) U.S. Cl.
CPC .............. *A61K 35/74* (2013.01); *A61K 35/745* (2013.01)

(58) Field of Classification Search
None
See application file for complete search history.

(56) References Cited

U.S. PATENT DOCUMENTS

2004/0071680 A1* 4/2004 Song et al. ............. 424/93.45
2004/0096427 A1 5/2004 Panigrahi
2005/0288250 A1* 12/2005 Rautonen et al. ............ 514/54
2006/0093592 A1* 5/2006 Cheruvanky et al. ...... 424/93.45
2008/0286254 A1 11/2008 Sakamoto

FOREIGN PATENT DOCUMENTS

| AU | WO 02/02138 | * 10/2002 | ............ A61K 39/02 |
|---|---|---|---|
| WO | WO 9629083 A1 | 9/1996 | |
| WO | WO 0202138 A1 | 1/2002 | |
| WO | WO 02062360 A1 | 8/2002 | |
| WO | WO 2009071086 | 6/2009 | |

OTHER PUBLICATIONS

Jie et al. "Studies on the effects of polydextrose intake on physiologic functions in Chinese people" Am J Clin Nutr 2000;72:1503-9.*
Danner et al. "Endotoxemia in Human Septic Shock" Chest / 99 / 1 / Jan. 1991, p. 169-175.*
Ma et al. "Probiotics improve high fat diet-induced hepatic steatosis and insulin resistance by increasing hepatic NKT cells" Journal of Hepatology 49 (2008) 821-830.*
International Preliminary Report on Patentability and Written Opinion of the International Searching Authority dated Feb. 9, 2012 for PCT/IB2010/053482, 9 pgs.
Cani Patrice D. et al: "Metabolic endotoxemia initiates obesity and insulin resistance." Diabetes, vol. 56, No. 7, Jul. 2007, pp. 1761-1772.
Antes TJ, et al., "Human apolipoprotein B gene intestinal control region," *Biochemistry*, 2001, vol. 40, pp. 6720-6730.
Brunham LR et al., "Intestinal ABCA1 directly contributes to HDL biogenesis in vivo," *J Clin Invest.*, 2006, vol. 116, p. 1052-1062.
Cani PD et al., "Role of gut microflora in the development of obesity and insulin resistance following high-fat diet feeding", *Pathol Biol* (Paris), 2008, vol. 56, No. 5, p. 305-309.
Cani PD et al., "Changes in gut microbiota control metabolic endotoxemia-induced inflammation in high-fat diet-induced obesity and diabetes in mice," *Diabetes*, 2008, vol. 57, p. 1470-1481.
Cani PD et al., "Selective increases of bifidobacteria in gut microflora improve high-fat-diet-induced diabetse in mice through a mechanism associated with endotoxaemia," *Diabetologia*, 2007, vol. 50, p. 2374-2383.
Gentleman RC et al. "Bioconductor: open software development for computational biology and bioinformatics", *Genome Biol.*, 2004, 5, R80.
Heilig HG. et al., "Molecular diversity of *Lactobacillus* spp. and other lactic acid bacteria in the human intestine as determined by specific amplification of 16S ribosomal DNA," *Applied Environmental Microbiology*, 2002, vol. 68, p. 114-123.
Iqbal J and Hussain MM, "Intestinal lipid absorption," *American Journal of Physiology-Endocrinology and Metabolism*, 2009, 296, E1183-E1194.
Knauf C et al., "Brain Glucogon-Like Peptide 1 Signaling Controls the onset of High-Fat Diet-Induced Insulin Resistance and Reduces Energy Expenditure," *Endocrinology*, 2008, vol. 149, p. 4768-4777.
Leng SY et al., "Hepatocyte nuclear factor-4 mediates apolipoprotein A-IV transcriptional regulation by fatty acid in newborn swine enterocytes," *American Journal of Physiology-Gastrointestinal and Liver Physiology*, 2007, vol. 293, G475-G483.
Makivuokko H. et al., "In Vitro Effects on Polydextrose by Colonic Bacteria and Caco-2 Cell Cyclooxygenase Gene Expression," *Nutrition and Cancer*, 2005, vol. 52, No. 1, p. 94-104.
Matsuda K. et al., "Sensitive Quantitative Detection of Commensal Bacteria by rRNA-Targeted Reverse Transcription-PCR," *Applied Environmental Microbiology*, 2007, 73, 32-39.

(Continued)

*Primary Examiner* — Thane Underdahl

(57) ABSTRACT

The invention relates to use of a bacterium selected from a lactic acid bacterium, a *Bifidobacterium* or a mixture of any thereof for treating metabolic endotoxemia, inhibiting bacterial translocation and regulating lipid absorption in a mammal.

14 Claims, 10 Drawing Sheets

(56) References Cited

OTHER PUBLICATIONS

Putaala H, et al. "Effect of four probiotic strains and *Escherichia coli* O157:H7 on tight junction integrity and cyclo-oxygenase expression", *Research in Microbiology*, 2008, vol. 159, No. 9-10, pp. 692-698.

Rinttilä T. et al., "Development of an extensive set of 16S rDNA-targeted primers for quantification of pathogenic and indigenous bacteria in faecal samples by real-time PCR," *J. Appl. Microbiol.*, 2004, 97, 1166-1177.

Schiffrin E.J. et al., "Probiotic yogurt in the elderly with intestinal bacterial overgrowth: endotoxaemia and innate immune functions," *British Journal of Nutrition*, 2009, vol. 1001, pp. 961-966.

Turini P. et al., "Insulin resistance in mice lacking neuronal nitric oxide synthase is related to the alpha-adrenergic mechanism," *Swiss Med. Weekly*, 2007, vol. 137, pp. 700-704.

Walter J. et al., "Detection of *Lactobacillus*, *Pediococcus*, *Leuconostoc*, and *Weissella* species in human feces by using group-specific PCR primers and denaturing gradient gel electrophoresis," *Applied Environmental Microbiology*, 2001, vol. 67, pp. 2578-2585.

von Bergmann K et al., "Cholesterol and Plant Sterol Absorption: Recent Insights," *American Journal of Cardiology*, 2005, vol. 96, No. 1A, P 10D-14D.

Bischoff, S. C., et al., "Intestinal permeability—a new target for disease prevention and therapy" *BMC Gastroenterology* (2014) 14, pp. 1-25.

Ghoshal, S., et al, "Chylomicrons promote intestinal absorption of lipopolysaccharides" *Journal of Lipid Research* (2009) 50, pp. 90-97.

Lopetuso, L. R., et al., "The theraeutic management of put barrier leaking: the emerging role for mucosal barrier protectors" *European Review for Medical and Parhmacolocial Sciences* (2015) vol. 19, pp. 1068-1076.

Moreira, A. P. B., et al., "Influence of a high-fat diet on gut microbiota, intestinal permeability and metabolic endotaxaemia" *Brifish Journal of Nutrition* (2012) vol. 108, pp. 801-809.

\* cited by examiner

▩ = Significant difference between normal chow group and high fat diet group (Student's t-test P-value < 0.05)

● = Significant difference between high fat diet group and high fat diet + probiotics groups (Student's t-test P-value < 0.05).

■ = Significant difference between normal chow group and high fat diet group (Student's t-test P-value<0.05);

● = Significant difference between high fat diet group and high fat diet + probiotics groups (Student's t-test P-value<0.05);

○ = Trend for a significant difference between high fat diet group and high fat diet + probiotics groups (Student's t-test 0.05< P-value< 0.15).

■ = Significant difference between normal chow group and high fat diet group (Student's t-test P-value<0.05).

■ = Significant difference between normal chow group and high fat diet group (Student's t-test P-value<0.05);

o = Trend for a significant difference between high fat diet group and high fat diet + probiotics groups (Student's t-test 0.05< P-value< 0.15).

□ = A trend for a significant difference between normal chow group and high fat diet group (Student's t-test 0.05<P-value< 0.15);
o = Trend for a significant difference between high fat diet group and high fat diet + probiotics groups (Student's t-test 0.05<P-value< 0.15).

▨ = Significant difference between normal chow group and high fat diet group (Student's t-test P-value<0.05);

○ = Trend for a significant difference between high fat diet group and high fat diet + probiotics groups (Student's t-test 0.05< P-value< 0.15).

LACTIC ACID BACTERIA AND BIFIDOBACTERIA FOR TREATING ENDOTOXEMIA

CLAIM FOR PRIORITY

This application claims priority under 35 U.S.C. 371 to International Application No. PCT/IB2010/053482, filed on Jul. 30, 2010, which claims priority to U.S. Patent Application No. 61/229,980, filed Jul. 30, 2009, U.S. Patent Application No. 61/312,400, filed Mar. 10, 2010, U.S. Patent Application No. 61/321,949, filed Apr. 8, 2010, and U.S. Patent Application No. 61/325,919, filed Apr. 20, 2010, each of which is hereby incorporated by reference in its entirety.

FIELD OF THE INVENTION

This invention relates to new uses of lactic acid bacteria and *Bifidobacteria*, (particularly, although not exclusively, probiotic bacteria), and to food products, feed products, dietary supplements and pharmaceutical formulations containing them.

BACKGROUND TO THE INVENTION

Endotoxemia is defined as the presence of an elevated level of lipopolysaccharides (also known as endotoxins) in the body. Lipopolysaccharides (LPS), also known as lipoglycans, are large molecules consisting of at least one lipid moiety and at least one polysaccharide moiety joined by a covalent bond. LPS are found in the outer membrane of Gram-negative bacteria, act as endotoxins and elicit strong immune responses in animals.

Cani et al., *Diabetes*, 2007, 56, 1761-1772, describes the induction of an increase in endotoxemia in mice fed a high-fat diet. The authors found that plasma LPS concentration varies throughout the day, increasing to a maximum at the end of the dark, feeding period for mice fed a normal diet, and that a high-fat diet caused endotoxemia to be high throughout the day. The authors define the term 'metabolic endotoxemia' as a chronic, 2- to 3-fold increase in plasma lipopolysaccharides (LPS) concentration from baseline levels, induced by a high-fat diet, and note that the endotoxemia levels reached was 10-50 times lower than that obtained during septic shock.

Bacterial translocation is defined as the passage of viable bacteria from the intestinal tract through the epithelial mucosa into the body. Bacteria may enter the lymphatic system via mesenteric lymph nodes and therefore may be circulated systemically. Bacteria can also enter blood circulation (bacteremia) and may also be located in tissues. Bacterial translocation may occur in a number of medical conditions, including intestinal bacterial overgrowth, intestinal injury and shock. Any medical condition associated with increased intestinal permeability can potentially lead to bacterial translocation.

As LPS originate from bacteria in the gut, translocation of bacteria from the gut into the body may potentially serve as a potential mechanism for endotoxemia, including metabolic endotoxemia. If Gram-negative bacteria translocate into the body, they serve as a source of LPS. However, the exact route of LPS into the body in metabolic endotoxemia is currently unknown: bacterial translocation is considered one possible explanation, but free LPS from the gut may also enter the body during normal lipid absorption. It is also possible that several mechanisms take place at the same time.

Schiffrin et al., *Br. J. Nutr.*, 2009, 101, 961-966, describe the use of a probiotic yogurt supplement in elderly patients with small-intestinal bacterial overgrowth (SIBO). The effects on intestinal colonisation, gut permeability, endotoxin translocation and modification of innate immune functions were assessed. However, the endotoxemia in the patients described in this document is septic shock endotoxemia, which is caused by infection with pathogens, such as pathogenic bacteria, and in which, as described in the Cani et al. article referred to above, plasma LPS levels are increased by a much larger factor from normal levels. This is distinct from metabolic endotoxemia, which as described above is generally caused by diet (in particular, by a high-fat diet) and in which the increase in plasma LPS levels (expressed as a multiple of normal levels) is much lower.

SUMMARY OF THE INVENTION

In one aspect, the invention provides use of a bacterium selected from a lactic acid bacterium, a *Bifidobacterium* or a mixture of any thereof in the manufacture of a food product, dietary supplement or medicament for treating metabolic endotoxemia in a mammal.

In another aspect, the invention provides use of a bacterium selected from the species *Lactobacillus acidophilus*, *Lactobacillus plantarum*, *Bifidobacterium animalis*, *Bifidobacterium lactis*, or *Bifidobacterium bifidium*, or a mixture of any thereof in the manufacture of a food product, dietary supplement or medicament for treating endotoxemia in a mammal.

In a further aspect, the invention provides use of a bacterium selected from a lactic acid bacterium, a *Bifidobacterium* or a mixture of any thereof in the manufacture of a food product, dietary supplement or medicament for inhibiting bacterial translocation in a mammal.

In a still further aspect, the invention provides use of a bacterium selected from a lactic acid bacterium, a *Bifidobacterium* or a mixture of any thereof in the manufacture of a food product, dietary supplement or medicament for treating infections caused by Gram-negative bacteria, treating overgrowth of Gram-negative bacteria, or treating an imbalance of intestinal and/or mucosal Gram-negative bacteria (in particular in the gastrointestinal tract) in a mammal.

In a yet further aspect, the invention provides use of a bacterium selected from a lactic acid bacterium, a *Bifidobacterium* or a mixture of any thereof in the manufacture of a food product, dietary supplement or medicament for treating translocation of Gram-negative bacteria in a mammal.

In a still further aspect, the invention provides use of a bacterium selected from a lactic acid bacterium, a *Bifidobacterium* or a mixture of any thereof in the manufacture of a food product, dietary supplement or medicament for reducing the elevated adhesion of Gram-negative or pathogenic bacteria to the gastrointestinal mucosa of a mammal.

In a yet further aspect, the invention provides use of a bacterium selected from a lactic acid bacterium, a *Bifidobacterium* or a mixture of any thereof in the manufacture of a food product, dietary supplement or medicament for treating endotoxemia in a mammal by reducing the elevated adhesion of Gram-negative or pathogenic bacteria to the gastrointestinal mucosa of said mammal.

In a still further aspect, the invention provides use of a bacterium selected from a lactic acid bacterium, a *Bifidobacterium* or a mixture of any thereof in the manufacture of a food product, dietary supplement or medicament for reducing the elevated adhesion of lipopolysaccharide-containing bacteria to the gastrointestinal mucosa of a mammal.

In a yet further aspect, the invention provides use of a bacterium selected from a lactic acid bacterium, a *Bifidobacterium* or a mixture of any thereof in the manufacture of a food product, dietary supplement or medicament for treating endotoxemia in a mammal by reducing the elevated adhesion of lipopolysaccharide-containing bacteria to the gastrointestinal mucosa of said mammal.

In a further aspect, the invention provides use of a bacterium selected from a lactic acid bacterium, a *Bifidobacterium* or a mixture of any thereof in the manufacture of a food product, dietary supplement or medicament for regulating lipid absorption in a mammal.

In a still further aspect, the invention provides use of a bacterium selected from a lactic acid bacterium, a *Bifidobacterium* or a mixture of any thereof in the manufacture of a food product, dietary supplement or medicament for treating endotoxemia in a mammal by regulating lipid absorption in said mammal.

In a still further aspect, the invention provides use of a bacterium selected from a lactic acid bacterium, a *Bifidobacterium* or a mixture of any thereof in the manufacture of a food product, dietary supplement or medicament for treating bacteremia in a mammal.

In a yet further aspect, the invention provides use of a combination of:
(a) a lactic acid bacterium, a Bifidobacterium or a mixture of any thereof; and
(b) a prebiotic;
in the manufacture of a food product, dietary supplement or medicament for treating endotoxemia in a mammal.

In a yet further aspect, the invention provides a bacterium selected from a lactic acid bacterium, a *Bifidobacterium* or a mixture of any thereof for use in treating metabolic endotoxemia in a mammal.

In a still further aspect, the invention provides a bacterium selected from the species *Lactobacillus acidophilus, Lactobacillus plantarum, Bifidobacterium animalis, Bifidobacterium lactis*, or *Bifidobacterium bifidum*, or a mixture of any thereof for use in treating endotoxemia in a mammal.

In a yet further aspect, the invention provides a bacterium selected from a lactic acid bacterium, a *Bifidobacterium* or a mixture of any thereof for use in inhibiting bacterial translocation in a mammal.

In a still further aspect, the invention provides a bacterium selected from a lactic acid bacterium, a *Bifidobacterium* or a mixture of any thereof for use in treating infections caused by Gram-negative bacteria, treating overgrowth of Gram-negative bacteria, or treating an imbalance of intestinal and/or mucosal Gram-negative bacteria (in particular in the gastrointestinal tract) in a mammal.

In a yet further aspect, the invention provides a bacterium selected from a lactic acid bacterium, a *Bifidobacterium* or a mixture of any thereof for use in treating translocation of Gram-negative bacteria in a mammal.

In a still further aspect, the invention provides a bacterium selected from a lactic acid bacterium, a *Bifidobacterium* or a mixture of any thereof for use in reducing the elevated adhesion of Gram-negative or pathogenic bacteria to the gastrointestinal mucosa of a mammal.

In a yet further aspect, the invention provides a bacterium selected from a lactic acid bacterium, a *Bifidobacterium* or a mixture of any thereof for use in treating endotoxemia in a mammal by reducing the elevated adhesion of Gram-negative or pathogenic bacteria to the gastrointestinal mucosa of said mammal.

In a still further aspect, the invention provides a bacterium selected from a lactic acid bacterium, a *Bifidobacterium* or a mixture of any thereof for use in reducing the elevated adhesion of lipopolysaccharide-containing bacteria to the gastrointestinal mucosa of a mammal.

In a yet further aspect, the invention provides a bacterium selected from a lactic acid bacterium, a *Bifidobacterium* or a mixture of any thereof for use in treating endotoxemia in a mammal by reducing the elevated adhesion of lipopolysaccharide-containing bacteria to the gastrointestinal mucosa of said mammal.

In a further aspect, the invention provides a bacterium selected from a lactic acid bacterium, a *Bifidobacterium* or a mixture of any thereof for use in regulating lipid absorption in a mammal.

In a still further aspect, the invention provides a bacterium selected from a lactic acid bacterium, a *Bifidobacterium* or a mixture of any thereof for use in treating endotoxemia in a mammal by regulating lipid absorption in said mammal.

In a yet further aspect, the invention provides a bacterium selected from a lactic acid bacterium, a *Bifidobacterium* or a mixture of any thereof for use in treating bacteremia in a mammal.

In a yet further aspect, the invention provides a combination of:
(a) a lactic acid bacterium, a *Bifidobacterium* or a mixture of any thereof; and
(b) a prebiotic;
for use in treating endotoxemia in a mammal.

In a still further aspect, the invention provides a method of treating metabolic endotoxemia in a mammal in need thereof, the method comprising administering an effective amount of a bacterium selected from a lactic acid bacterium, a *Bifidobacterium* or a mixture of any thereof.

In a yet further aspect, the invention provides a method of treating endotoxemia in a mammal in need thereof, the method comprising administering an effective amount of a bacterium selected from the species *Lactobacillus acidophilus, Lactobacillus plantarum, Bifidobacterium animalis, Bifidobacterium lactis*, or *Bifidobacterium bifidium*, or a mixture of any thereof.

In a yet further aspect, the invention provides a method of inhibiting bacterial translocation in a mammal in need thereof, the method comprising administering an effective amount of a bacterium selected from a lactic acid bacterium, a *Bifidobacterium* or a mixture of any thereof.

In a still further aspect, the invention provides a method of treating infections caused by Gram-negative bacteria, treating overgrowth of Gram-negative bacteria, or treating an imbalance of intestinal and/or mucosal Gram-negative bacteria (in particular in the gastrointestinal tract) in a mammal in need thereof, the method comprising administering an effective amount of a bacterium selected from a lactic acid bacterium, a *Bifidobacterium* or a mixture of any thereof.

In a yet further aspect, the invention provides a method of treating translocation of Gram-negative bacteria in a mammal in need thereof, the method comprising administering an effective amount of a bacterium selected from a lactic acid bacterium, a *Bifidobacterium* or a mixture of any thereof.

In a still further aspect, the invention provides a method of reducing the elevated adhesion of Gram-negative or pathogenic bacteria to the gastrointestinal mucosa in a mammal in need thereof, the method comprising administering an effective amount of a bacterium selected from a lactic acid bacterium, a *Bifidobacterium* or a mixture of any thereof.

In a yet further aspect, the invention provides a method of treating endotoxemia in a mammal in need thereof by reducing the elevated adhesion of Gram-negative or pathogenic bacteria to the gastrointestinal mucosa of said mammal, the method comprising administering an effective amount of a bacterium selected from a lactic acid bacterium, a *Bifidobacterium* or a mixture of any thereof.

In a still further aspect, the invention provides a method of reducing the elevated adhesion of lipopolysaccharide-containing bacteria to the gastrointestinal mucosa of a mammal in need thereof, the method comprising administering an effective amount of a bacterium selected from a lactic acid bacterium, a *Bifidobacterium* or a mixture of any thereof.

In a yet further aspect, the invention provides a method of treating endotoxemia in a mammal in need thereof by reducing the elevated adhesion of lipopolysaccharide-containing bacteria to the gastrointestinal mucosa of said mammal, the method comprising administering an effective amount of a bacterium selected from a lactic acid bacterium, a *Bifidobacterium* or a mixture of any thereof.

In a still further aspect, the invention provides a method of regulating lipid absorption in a mammal in need thereof, the method comprising administering an effective amount of a bacterium selected from a lactic acid bacterium, a *Bifidobacterium* or a mixture of any thereof.

In a yet further aspect, the invention provides a method of treating endotoxemia in a mammal in need thereof by regulating lipid absorption in said mammal, the method comprising administering an effective amount of a bacterium selected from a lactic acid bacterium, a *Bifidobacterium* or a mixture of any thereof.

In a still further aspect, the invention provides a method of treating bacteremia in a mammal in need thereof, the method comprising administering an effective amount of a bacterium selected from a lactic acid bacterium, a *Bifidobacterium* or a mixture of any thereof.

DETAILED DESCRIPTION OF THE INVENTION

Lactic Acid Bacteria and *Bifidobacteria*

Figure 1:
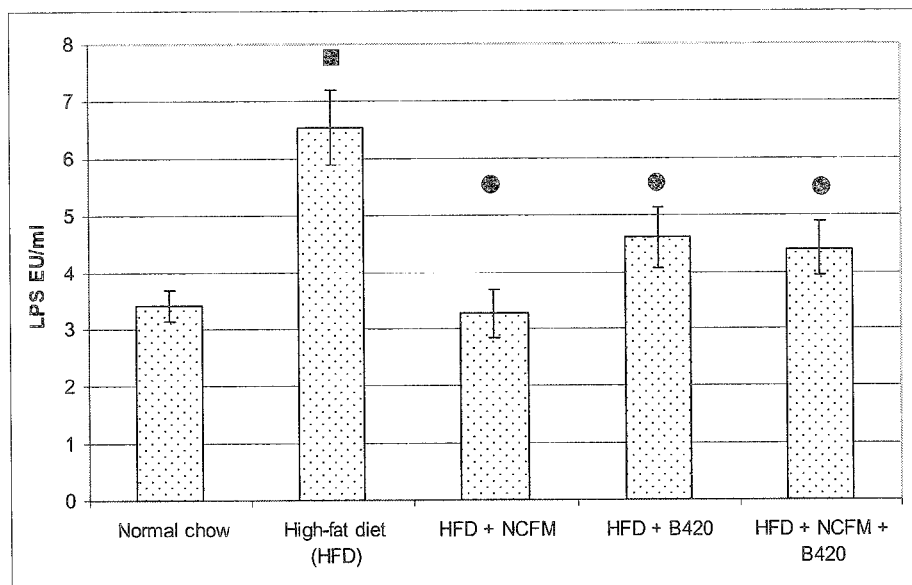
FIG. 1 illustrates the level of plasma LPS (endotoxemia) in mice administered with normal chow (NC), high fat diet (HFD), or high fat diet supplemented with bacteria according to the present invention, namely *Lactobacillus acidophilus* strain NCFM (NCFM), *Bifidobacterium animalis* subsp. *lactis* strain 420 (B420) or a combination of the two (NCFM+B420)

The bacterium used in embodiments of the present invention is selected from a lactic acid bacterium (LAB), a *Bifidobacterium* or a mixture of any thereof. In this specification the term 'lactic acid bacterium' includes any bacterium capable of producing, as the major metabolic end product of carbohydrate fermentation, lactic acid or at least one of its derivatives (including, but not limited to, acetic acid or propionic acid): the term is therefore intended to include propionic acid bacteria (PAB), which produce propionic acid as a carbohydrate fermentation product.

The bacterium may be used in any form capable of exerting the effects described herein. For example, the bacteria may be viable, dormant, inactivated or dead bacteria. Preferably, the bacteria are viable bacteria.

The bacteria may comprise whole bacteria or may comprise bacterial components. Examples of such components include bacterial cell wall components such as peptidoglycan, bacterial nucleic acids such as DNA and RNA, bacterial membrane components, and bacterial structural components such as proteins, carbohydrates, lipids and combinations of these such as lipoproteins, glycolipids and glycoproteins.

The bacteria may also or alternatively comprise bacterial metabolites. In this specification the term 'bacterial metabolites' includes all molecules produced or modified by the (probiotic) bacteria as a result of bacterial metabolism during growth, survival, persistence, transit or existence of bacteria during probiotic product manufacture and storage and during gastrointestinal transit in a mammal. Examples include all organic acids, inorganic acids, bases, proteins and peptides, enzymes and co-enzymes, amino acids and nucleic acids, carbohydrates, lipids, glycoproteins, lipoproteins, glycolipids, vitamins, all bioactive compounds, metabolites containing an inorganic component, and all small molecules, for example nitrous molecules or molecules containing a sulphurous acid.

Preferably the bacteria comprise whole bacteria, more preferably whole viable bacteria.

Preferably the lactic acid bacterium and/or *Bifidobacterium* to be used in the present invention is a lactic acid bacterium and/or *Bifidobacterium* which is generally recognised as safe and, which is preferably GRAS approved.

A skilled person will readily be aware of specific species and or strains of lactic acid bacteria and/or *Bifidobacteria* from within the genera described herein which are used in the food and/or agricultural industries and which are generally considered suitable for human and/or animal consumption.

Preferably, the lactic acid bacterium and/or *Bifidobacterium* used in accordance with the present invention is one which is suitable for human and/or animal consumption.

In the present invention, the bacteria used may be of the same type (genus, species and strain) or may comprise a mixture of genera, species and/or strains.

Suitable lactic acid bacteria may be selected from the genera *Lactococcus, Lactobacillus, Leuconostoc, Carnobacterium, Enterococcus, Propionibacterium, Pediococcus*, and *Streptococcus* and mixtures thereof. Typically, the lactic acid bacteria are selected from the species *Leuconostoc* spp., *Lactococcus cremoris, Lactococcus lactis, Lactobacillus acidophilus, Lactobacillus casei, Lactobacillus kefiri, Lactobacillus bifidus, Lactobacillus brevis, Lactobacillus helveticus, Lactobacillus paracasei, Lactobacillus rhamnosus, Lactobacillus salivarius, Lactobacillus curvatus, Lactobacillus bulgaricus, Lactobacillus sakei, Lactobacillus reuteri, Lactobacillus fermentum, Lactobacillus farciminis, Lactobacillus lactis, Lactobacillus delbreuckii, Lactobacillus plantarum, Lactobacillus paraplantarum, Lactobacillus crispatus, Lactobacillus gasseri, Lactobacillus johnsonii* and *Lactobacillus jensenii*, and combinations of any thereof.

Suitable *Bifidobacteria* are selected from the species *Bifidobacterium lactis, Bifidobacterium bifidium, Bifidobacterium longum, Bifidobacterium animalis, Bifidobacterium breve, Bifidobacterium infantis, Bifidobacterium catenulatum, Bifidobacterium pseudocatenulatum, Bifidobacterium adolescentis*, and *Bifidobacterium angulatum*, and combinations of any thereof.

Preferably, the bacteria used in the present invention are selected from the genera *Lactobacillus* or *Bifidobacterium* and mixtures thereof. More preferably, the bacteria used in the present invention are selected from the species *Lactobacillus acidophilus, Lactobacillus plantarum, Lactobacillus salivarius, Bifidobacterium animalis, Bifidobacterium lactis*, or *Bifidobacterium bifidium*, and mixtures thereof. A combination of bacteria of the species *Lactobacillus acidophilus* and bacteria of the species *Bifidobacterium animalis* is especially preferred.

In a particularly preferred embodiment, the bacteria used in the present invention are *Lactobacillus acidophilus* strain NCFM. *Lactobacillus acidophilus* NCFM is commercially available from Danisco A/S under the name HOWARU™ Dophilus.

In an alternative particularly preferred embodiment, the bacteria used in the present invention are *Bifidobacterium animalis* subsp. *lactis* strain 420 (B420), This strain is commercially available from Danisco A/S.

In an alternative particularly preferred embodiment, the bacteria used in the present invention are *Lactobacillus salivarius* strain 33 (Ls-33). This strain is commercially available from Danisco A/S.

In one embodiment, the bacterium used in the present invention is a probiotic bacterium. In this specification the term 'probiotic bacterium' is defined as covering any non-pathogenic bacterium which, when administered live in adequate amounts, confer a health benefit on the host. These probiotic strains generally have the ability to survive the passage through the upper part of the digestive tract. They are non-pathogenic, non-toxic and exercise their beneficial effect on health on the one hand via ecological interactions with the resident flora in the digestive tract, and on the other hand via their ability to influence the immune system in a positive manner via the "GALT" (gut-associated lymphoid tissue). Depending on the definition of probiotics, these bacteria, when given in a sufficient number, have the ability to progress live through the intestine, however they do not cross the intestinal barrier and their primary effects are therefore induced in the lumen and/or the wall of the gastrointestinal tract. They then form part of the resident flora during the administration period. This colonization (or transient colonization) allows the probiotic bacteria to exercise a beneficial effect, such as the repression of potentially pathogenic microorganisms present in the flora and interactions with the immune system of the intestine.

In preferred embodiments, the bacterium used in the present invention is a probiotic lactic acid bacterium and/or a probiotic *Bifidobacterium*.

in some preferred embodiments, the *Bifidobacterium* is used in the present invention together with a bacterium of the genus *Lactobacillus*. A combination of *Bifidobacterium* and *Lactobacillus* bacteria according to the present invention exhibits a synergistic effect in certain applications (i.e. an effect which is greater than the additive effect of the bacteria when used separately). For example, combinations which, in addition to having effect on the mammal as single components, may have beneficial effect on the other components of the combination, for example by producing metabolites which are then in turn used as an energy source by other components of the combination, or maintaining physiological conditions which favour the other components.

Typically, the *Lactobacillus* bacteria used in the combination are selected from the species *Lactobacillus acidophilus, Lactobacillus casei, Lactobacillus kefiri, Lactobacillus bifidus, Lactobacillus brevis, Lactobacillus helveticus, Lactobacillus paracasei, Lactobacillus rhamnosus, Lactobacillus salivarius, Lactobacillus curvatus, Lactobacillus bulgaricus, Lactobacillus sakei, Lactobacillus reuteri, Lactobacillus fermentum, Lactobacillus farciminis, Lactobacillus lactis, Lactobacillus delbreuckii, Lactobacillus plantarum, Lactobacillus paraplantarum, Lactobacillus crispatus, Lactobacillus gasseri, Lactobacillus johnsonii* and *Lactobacillus jensenii*, and combinations of any thereof.

In preferred embodiments, the *Lactobacillus* bacterium used in the present invention is a probiotic *Lactobacillus*.

Preferably, the *Lactobacillus* bacterium used in the present invention of the species *Lactobacillus acidophilus*.

In a particularly preferred embodiment, the bacteria used in the present invention comprise a combination of *Bifidobacterium animalis* subsp. *lactis* strain 420 (B420) and *Lactobacillus acidophilus* strain NCFM.

Dosage

The lactic acid bacterium and/or *Bifidobacterium* used in accordance with the present invention (such as a strain of *Lactobacillus* spp.; for example a strain of *Lactobacillus acidophilus, Lactobacillus salivarius* and/or *Lactobacillus plantarum*, such as a strain of *Lactobacillus acidophilus* or *Lactobacillus salivarius*, for example *Lactobacillus acidophilus* strain NCFM or *Lactobacillus salivarius* strain 33) and/or a strain of *Bifidobacterium* spp., such as a strain of *Bifidobacterium animalis* subsp. *lactis*, for example *Bifidobacterium animalis* subsp. *lactis* strain 420 (B420)), may comprise from $10^6$ to $10^{12}$ CFU of bacteria/g of support, and more particularly from $10^8$ to $10^{12}$ CFU of bacteria/g of support, preferably $10^9$ to $10^{12}$ CFU/g for the lyophilized form.

Suitably the lactic acid bacterium and/or *Bifidobacterium* used in accordance with the present invention (such as a strain of *Lactobacillus* spp.; for example a strain of *Lactobacillus acidophilus, Lactobacillus salivarius* and/or *Lactobacillus plantarum*, such as a strain of *Lactobacillus acidophilus* or *Lactobacillus salivarius*, for example *Lactobacillus acido-*

*philus* strain NCFM or *Lactobacillus salivarius* strain 33) and/or a strain of *Bifidobacterium* spp., such as a strain of *Bifidobacterium animalis* subsp. *lactis*, for example *Bifidobacterium animalis* subsp. lactis strain 420 (B420)), may be administered at a dosage of from about $10^6$ to about $10^{12}$ CFU of microorganism/dose, preferably about $10^8$ to about $10^{12}$ CFU of microorganism/dose. By the term "per dose" it is meant that this amount of microorganism is provided to a subject either per day or per intake, preferably per day. For example, if the microorganism is to be administered in a food product (for example in a yoghurt)—then the yoghurt will preferably contain from about $10^8$ to $10^{12}$ CFU of the microorganism. Alternatively, however, this amount of microorganism may be split into multiple administrations each consisting of a smaller amount of microbial loading—so long as the overall amount of microorganism received by the subject in any specific time (for instance each 24 hour period) is from about $10^6$ to about $10^{12}$ CFU of microorganism, preferably $10^8$ to about $10^{12}$ CFU of microorganism.

In accordance with the present invention an effective amount of at least one strain of a microorganism may be at least $10^6$ CFU of microorganism/dose, preferably from about $10^6$ to about $10^{12}$ CFU of microorganism/dose, preferably about $10^8$ to about $10^{12}$ CFU of microorganism/dose.

In one embodiment, preferably the lactic acid bacterium and/or *Bifidobacterium* used in accordance with the present invention (such as a strain of *Lactobacillus* spp.; for example a strain of *Lactobacillus acidophilus, Lactobacillus salivarius* and/or *Lactobacillus plantarum* and/or a strain of *Bifidobacterium* spp., such as a strain of *Lactobacillus acidophilus* or *Lactobacillus salivarius*, for example *Lactobacillus acidophilus* strain NCFM or *Lactobacillus salivarius* strain 33) such as a strain of *Bifidobacterium animalis* subsp. *lactis*, for example *Bifidobacterium animalis* subsp. *lactis* strain 420 (B420)) may be administered at a dosage of from about $10^6$ to about $10^{12}$ CFU of microorganism/day, preferably about $10^8$ to about $10^{12}$ CFU of microorganism/day. Hence, the effective amount in this embodiment may be from about $10^6$ to about $10^{12}$ CFU of microorganism/day, preferably about $10^8$ to about $10^{12}$ CFU of microorganism/day.

CFU stands for "colony-forming units". By 'support' is meant the food product, dietary supplement or the pharmaceutically acceptable support.

Subjects/Medical Indications

The lactic acid bacteria and/or *Bifidobacteria* to which the present invention relates are administered to a mammal, including for example livestock (including cattle, horses, pigs, chickens and sheep), and humans. In some aspects of the present invention the mammal is a companion animal (including pets), such as a dog or a cat for instance. In some aspects of the present invention, the subject may suitably be a human.

The inventors have surprisingly found that the lactic acid bacteria and/or *Bifidobacteria* to which the present invention relates are capable of lowering blood plasma lipopolysaccharides (LPS) levels. This finding confers the potential for the bacteria to be useful in the treatment of endotoxemia, in particular metabolic endotoxemia.

LPS is a major cell wall component of gram-negative bacteria, which occurs in the intestine as a component of gram-negative microbiota but also as free LPS. Reduction of metabolic endotoxemia may result from reduction of translocation of gram-negative bacteria into the host, reduction of absorption of free LPS by the host, or enhanced clearance of LPS by the host.

In this specification, the term 'endotoxemia' when used alone means the presence of an elevated level of lipopolysaccharides (also known as endotoxins) in the body (particularly, although not exclusively, in blood plasma) when compared with basal lipopolysaccharide levels. The term 'endotoxemia' when used alone is intended to encompass both metabolic endotoxemia, defined in more detail below, and endotoxemia of other etiologies, such as endotoxemia caused by pathogenic infections (especially bacterial infections) or endotoxemia caused by small-intestinal bacterial overgrowth (SIBO).

In some embodiments, the lactic acid bacteria and/or *Bifidobacteria* to which the present invention relates are used to treat metabolic endotoxemia. In one aspect, the term 'metabolic endotoxemia' means endotoxemia (as defined above) induced by a high-fat diet. The term 'high-fat diet' is defined in more detail below.

In one aspect, the term 'metabolic endotoxemia' means an increase of the level of lipopolysaccharides in the mammalian body (particularly, although not exclusively, in blood plasma) by a factor ranging from 1.5 to 20, preferably 2 to 10, such as 2 to 4, preferably 2 to 3.5, compared with basal (normal) mammalian lipopolysaccharide levels. The increase in lipopolysaccharide levels is typically measured by the Limulus amaebocyte assay, a test well known to those skilled in the art.

In contrast, in the case of endotoxemia caused by pathogenic infections, such as bacterial infections (septic shock endotoxemia), LPS levels in the mammalian body, especially the human body (particularly, although not exclusively, in blood) are typically raised by a factor of greater than 20, such as greater than 30, preferably greater than 50, such as greater than 70, such as greater than 100, such as greater than 150, such as greater than 200 times compared with basal (normal) mammalian lipopolysaccharide levels.

Basal levels of lipopolysaccharides in humans are typically in the range of 1-2 Endotoxin Units (EU) per ml, as measured by the Limulus amaebocyte assay, an example of which is the Limulus amaebocyte extract assay with Kinetic-QCL test (Bio Whittaker, Cambrex BioScience).

Therefore in an alternative aspect, the term 'metabolic endotoxemia' means a level of lipopolysaccharides in the body (particularly, although not exclusively, in blood plasma) ranging from 1.5 to 40, preferably 2 to 20, such as 2 to 8, preferably 2 to 7, Endotoxin Units (EU)/ml, as measured by the Limulus amaebocyte extract assay.

In contrast, in the case of endotoxemia caused by pathogenic infections, such as bacterial infections (septic shock endotoxemia), LPS levels in the mammalian body, especially the human body (particularly, although not exclusively, in blood) are typically greater than 40, such as greater than 60, preferably greater than 100, such as greater than 140, such as greater than 200, such as greater than 300, such as greater than 400 EU/ml, as measured by the Limulus amaebocyte extract assay.

The present inventors have also surprisingly found that the lactic acid bacteria and/or *Bifidobacteria* to which the present invention relates can reduce the level of bacteria in metabolically very important tissues, the mesenteric adipose tissue, subcutaneous adipose tissue, mesenteric ganglion and subcutaneous ganglion, and the liver and spleen. This confers the potential for lactic acid bacteria and/or *Bifidobacteria* to which the present invention relates to be used for preventing or treating bacterial translocation into tissues and preventing or treating metabolic endotoxemia.

In particularly preferred embodiments, the lactic acid bacteria and/or *Bifidobacteria* to which the present invention relates may be used to reduce the levels of bacteria of the family Enterobacteriaceae in the mesenteric adipose tissue and the class Bacteriodetes in the liver tissue. These two major bacterial groups contain LPS as a component of bacterial cell wall and therefore act as potential source of elevated plasma LPS, which is associated with metabolic endotoxemia. These tissues play particularly important role in metabolic endotoxemia and other metabolic diseases, since LPS causes inflammation in these tissues, potentially leading to a cascade of adverse events including impaired glucose metabolism and reduced insulin sensitivity.

The present inventors have also surprisingly found that the lactic acid bacteria and/or *Bifidobacteria* to which the present invention relates are capable of regulating lipid absorption. Without wishing to be bound by theory, it is believed that, as LPS are carried primarily in lipids, regulating lipid absorption reduces the amount of bacteria and therefore the amount of LPS passing the intestinal barrier. This confers the potential for lactic acid bacteria and/or *Bifidobacteria* to which the present invention relates to be used for preventing the passage of LPS into tissues and therefore preventing or treating metabolic endotoxemia.

In addition, the present inventors have surprisingly found that the lactic acid bacteria and/or *Bifidobacteria* to which the present invention relates are capable of reducing elevated gram-negative bacterial adhesion in the gastrointestinal tract. Without wishing to be bound by theory, it is believed that reducing the elevated gram-negative bacterial adhesion reduces the amount of bacteria and therefore the amount of LPS passing the intestinal barrier. This confers the potential for lactic acid bacteria and/or *Bifidobacteria* to which the present invention relates to be used for preventing the passage of LPS into tissues and therefore preventing or treating metabolic endotoxemia.

The lactic acid bacteria and/or *Bifidobacteria* to which the present invention relates are suitable for administration to both diabetic and obese mammals. They could also be suitable for diabetic and non-obese mammals, as well as to obese mammals possessing the risk factors for diabetes, but not yet in a diabetic state. This aspect is discussed in more detail below.

In preferred embodiments, the condition being treated or prevented is diet-induced and/or diet-associated. The present inventors have surprisingly found that the lactic acid bacteria and/or *Bifidobacteria* can be used in accordance with the present invention to treat a number of diet-induced and/or diet-associated conditions, as described in more detail herein.

In particular, the use of lactic acid bacteria and/or *Bifidobacteria* according to the present invention is suitable for the treatment of mammals ingesting a high-fat diet. This aspect is discussed in more detail below.

The compositions are suitable for use in obese and diabetic patients. In this specification the term 'diabetes' includes all forms of diabetes which, as noted above, is characterised by disordered metabolism and abnormally high blood sugar (hyperglycaemia) resulting from insufficient levels of the hormone insulin. The term therefore includes Type 1 diabetes, Type 2 diabetes, gestational diabetes, and impaired glucose tolerance. Type 1 diabetes is characterised by loss of the insulin-producing beta cells of the islets of Langerhans in the pancreas, leading to a deficiency of insulin. Type 2 diabetes mellitus is characterised by insulin resistance or reduced insulin sensitivity, combined with reduced insulin secretion. Gestational diabetes is formally defined as "any degree of glucose intolerance with onset or first recognition during pregnancy". Impaired Glucose Tolerance (IGT) is a pre-diabetic state of dysglycemia that is associated with insulin resistance and increased risk of cardiovascular pathology. According to the criteria of the World Health Organization and the American Diabetes Association, impaired glucose tolerance is defined as two-hour glucose levels of 140 to 199 mg per dL (7.8 to 11.0 mmol) on the 75-g oral glucose tolerance test. A patient is said to be under the condition of IGT when he/she has an intermediately raised glucose level after 2 hours, but less than would qualify for type 2 diabetes mellitus. The fasting glucose may be either normal or mildly elevated. IGT may precede type 2 diabetes mellitus by many years. IGT is also a risk factor for mortality.

In this specification, the term obesity is linked to body mass index (BMI). The body mass index (BMI) (calculated as weight in kilograms divided by the square of height in metres) is the most commonly accepted measurement for overweight and/or obesity. A BMI exceeding 25 is considered overweight. Obesity is defined as a BMI of 30 or more, with a BMI of 35 or more considered as serious comorbidity obesity and a BMI of 40 or more considered morbid obesity.

As noted above, the term "obesity" as used herein includes obesity, comorbidity obesity and morbid obesity. Therefore, the term "obese" as used here may be defined as a subject having a BMI of more than or equal to 30. In some embodiments, suitably an obese subject may have a BMI of more than or equal to 30, suitably 35, suitably 40.

While the composition of the invention is particularly suitable for use in patients who are both diabetic and obese, the composition is also suitable for those who are diabetic but not obese. It may also be suitable for use in obese patients possessing the risk factors for diabetes, but not yet in a diabetic state, as it could be expected that an obese person (but not diabetic), could limit the metabolic consequences of his obesity, i.e. the diabetes or at least insulino-resistance development.

In this specification the term "treatment" or "treating" refers to any administration of the lactic acid bacteria and/or *Bifidobacteria* according to the present invention and includes: (1) preventing the specified disease from occurring in an animal which may be predisposed to the disease but does not yet experience or display the pathology or symptomatology of the disease (including prevention of one or more risk factors associated with the disease); (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

Diet

As noted above, diabetic and/or obese mammals treated with bacteria according to the present invention may continue to ingest a high-fat diet while mitigating the metabolic consequences of their condition(s). In this specification the term 'high-fat diet' means a diet generally containing at least 20%, preferably at least 25%, such as at least 30%, for example at least 35%, such as at least 40%, for example at least 45%, such as at least 50%, for example at least 55%, such as at least 60%, for example at least 65%, such as at least 70%, for example at least 75%, such as at least 80%, for example at least 85%, such as at least 90% of calories from fat.

In some embodiments, diabetic and/or obese mammals treated with bacteria according to the present invention may ingest a high-carbohydrate diet while mitigating the metabolic consequences of their condition(s). In this specification the term 'high-carbohydrate diet' means a diet generally containing at least 50%, for example at least 55%, such as at least 60%, for example at least 65%, such as at least 70%, for example at least 75%, such as at least 80%, for example at least 85%, such as at least 90% of calories from carbohydrate.

Compositions

While is it possible to administer lactic acid bacteria and/or *Bifidobacteria* alone according to the present invention, the lactic acid bacteria and/or *Bifidobacteria* are typically and preferably administered on or in a support as part of a product, in particular as a component of a food product, a dietary supplement or a pharmaceutical formulation. These products typically contain additional components well known to those skilled in the art.

Any product which can benefit from the composition may be used in the present invention. These include but are not limited to foods, particularly fruit conserves and dairy foods and dairy food-derived products, and pharmaceutical products. The lactic acid bacteria may be referred to herein as "the composition of the present invention" or "the composition".

Food

In one embodiment, the lactic acid bacteria and/or *Bifidobacteria* are employed according to the invention in a food product such as a food supplement, a drink or a powder based on milk. Here, the term "food" is used in a broad sense—and covers food for humans as well as food for animals (i.e. a feed). In a preferred aspect, the food is for human consumption.

The food may be in the form of a solution or as a solid— depending on the use and/or the mode of application and/or the mode of administration.

When used as, or in the preparation of, a food, such as functional food, the composition of the present invention may be used in conjunction with one or more of: a nutritionally acceptable carrier, a nutritionally acceptable diluent, a nutritionally acceptable excipient, a nutritionally acceptable adjuvant, a nutritionally active ingredient.

By way of example, the composition of the present invention can be used as an ingredient to soft drinks, a fruit juice or a beverage comprising whey protein, health teas, cocoa drinks, milk drinks and lactic acid bacteria drinks, yoghurt and drinking yoghurt, cheese, ice cream, water ices and desserts, confectionery, biscuits cakes and cake mixes, snack foods, balanced foods and drinks, fruit fillings, care glaze, chocolate bakery filling, cheese cake flavoured filling, fruit flavoured cake filling, cake and doughnut icing, instant bakery filling creams, fillings for cookies, ready-to-use bakery filling, reduced calorie filling, adult nutritional beverage, acidified soy/juice beverage, aseptic/retorted chocolate drink, bar mixes, beverage powders, calcium fortified soy/plain and chocolate milk, calcium fortified coffee beverage.

The composition can further be used as an ingredient in food products such as American cheese sauce, anti-caking agent for grated & shredded cheese, chip dip, cream cheese, dry blended whip topping fat free sour cream, freeze/thaw dairy whipping cream, freeze/thaw stable whipped tipping, low fat and light natural cheddar cheese, low fat Swiss style yoghurt, aerated frozen desserts, hard pack ice cream, label friendly, improved economics & indulgence of hard pack ice cream, low fat ice cream: soft serve, barbecue sauce, cheese dip sauce, cottage cheese dressing, dry mix Alfredo sauce, mix cheese sauce, dry mix tomato sauce and others.

The term "dairy product" as used herein is meant to include a medium comprising milk of animal and/or vegetable origin. As milk of animal origin there can be mentioned cow's, sheep's, goat's or buffalo's milk. As milk of vegetable origin there can be mentioned any fermentable substance of vegetable origin which can be used according to the invention, in particular originating from soybeans, rice or cereals.

Still more preferably the food product employed according to the invention is a fermented milk or humanized milk.

For certain aspects, preferably the present invention may be used in connection with yoghurt production, such as fermented yoghurt drink, yoghurt, drinking yoghurt, cheese, fermented cream, milk based desserts and others.

Suitably, the composition can be further used as an ingredient in one or more of cheese applications, meat applications, or applications comprising protective cultures.

The present invention also provides a method of preparing a food or a food ingredient, the method comprising admixing the composition according to the present invention with another food ingredient.

Advantageously, the present invention relates to products that have been contacted with the composition of the present invention (and optionally with other components/ingredients), wherein the composition is used in an amount to be capable of improving the nutrition and/or health benefits of the product.

As used herein the term "contacted" refers to the indirect or direct application of the composition of the present invention to the product. Examples of the application methods which may be used, include, but are not limited to, treating the product in a material comprising the composition, direct application by mixing the composition with the product, spraying the composition onto the product surface or dipping the product into a preparation of the composition.

Where the product of the invention is a foodstuff, the composition of the present invention is preferably admixed with the product. Alternatively, the composition may be included in the emulsion or raw ingredients of a foodstuff. In a further alternative, the composition may be applied as a seasoning, glaze, colorant mixture, and the like.

For some applications, it is important that the composition is made available on or to the surface of a product to be affected/treated. This allows the composition to impart one or more of the following favourable characteristics: nutrition and/or health benefits.

The compositions of the present invention may be applied to intersperse, coat and/or impregnate a product with a controlled amount of a viable microorganism.

Preferably, the composition is used to ferment milk or sucrose fortified milk or lactic media with sucrose and/or maltose where the resulting media containing all components of the composition—i.e. said microorganism according to the present invention—can be added as an ingredient to yoghurt milk in suitable concentrations—such as for example in concentrations in the final product which offer a daily dose of $10^6$-$10^{10}$ cfu. The microorganism according to the present invention may be used before or after fermentation of the yoghurt.

For some aspects the microorganisms according to the present invention are used as, or in the preparation of, animal feeds, such as livestock feeds, in particular poultry (such as chicken) feed, or pet food.

Advantageously, where the product is a food product, the lactic acid bacteria should remain effective through the normal "sell-by" or "expiration" date during which the food product is offered for sale by the retailer. Preferably, the effective time should extend past such dates until the end of the normal freshness period when food spoilage becomes apparent. The desired lengths of time and normal shelf life will vary from foodstuff to foodstuff and those of ordinary skill in the art will recognise that shelf-life times will vary upon the type of foodstuff, the size of the foodstuff, storage temperatures, processing conditions, packaging material and packaging equipment.

Food Ingredient

The composition of the present invention may be used as a food ingredient and/or feed ingredient.

As used herein the term "food ingredient" or "feed ingredient" includes a formulation which is or can be added to functional foods or foodstuffs as a nutritional supplement.

The food ingredient may be in the form of a solution or as a solid—depending on the use and/or the mode of application and/or the mode of administration.

Food Supplements

The composition of the present invention may be—or may be added to—food supplements (also referred to herein as dietary supplements).

Functional Foods

The composition of the present invention may be—or may be added to—functional foods.

As used herein, the term "functional food" means food which is capable of providing not only a nutritional effect, but is also capable of delivering a further beneficial effect to consumer.

Accordingly, functional foods are ordinary foods that have components or ingredients (such as those described herein) incorporated into them that impart to the food a specific functional—e.g. medical or physiological benefit—other than a purely nutritional effect.

Although there is no legal definition of a functional food, most of the parties with an interest in this area agree that they are foods marketed as having specific health effects beyond basic nutritional effects.

Some functional foods are nutraceuticals. Here, the term "nutraceutical" means a food which is capable of providing not only a nutritional effect and/or a taste satisfaction, but is also capable of delivering a therapeutic (or other beneficial) effect to the consumer. Nutraceuticals cross the traditional dividing lines between foods and medicine.

Medicament

The term "medicament" as used herein encompasses medicaments for both human and animal usage in human and veterinary medicine. In addition, the term "medicament" as used herein means any substance which provides a therapeutic and/or beneficial effect. The term "medicament" as used herein is not necessarily limited to substances which need Marketing Approval, but may include substances which can be used in cosmetics, nutraceuticals, food (including feeds and beverages for example), probiotic cultures, and natural remedies. In addition, the term "medicament" as used herein encompasses a product designed for incorporation in animal feed, for example livestock feed and/or pet food.

Pharmaceutical

The composition of the present invention may be used as—or in the preparation of a pharmaceutical. Here, the term "pharmaceutical" is used in a broad sense—and covers pharmaceuticals for humans as well as pharmaceuticals for animals (i.e. veterinary applications). In a preferred aspect, the pharmaceutical is for human use and/or for animal husbandry.

The pharmaceutical can be for therapeutic purposes—which may be curative or palliative or preventative in nature. The pharmaceutical may even be for diagnostic purposes.

A pharmaceutically acceptable support may be for example a support in the form of compressed tablets, tablets, capsules, ointments, suppositories or drinkable solutions. Other suitable forms are provided below.

When used as—or in the preparation of—a pharmaceutical, the composition of the present invention may be used in conjunction with one or more of: a pharmaceutically acceptable carrier, a pharmaceutically acceptable diluent, a pharmaceutically acceptable excipient, a pharmaceutically acceptable adjuvant, a pharmaceutically active ingredient.

The pharmaceutical may be in the form of a solution or as a solid—depending on the use and/or the mode of application and/or the mode of administration.

The lactic acid bacteria and/or *Bifidobacteria* to which the present invention relates may be used as pharmaceutical ingredients. Here, the composition may be the sole active component or it may be at least one of a number (i.e. 2 or more) of active components.

The pharmaceutical ingredient may be in the form of a solution or as a solid—depending on the use and/or the mode of application and/or the mode of administration.

The lactic acid bacteria and/or *Bifidobacteria* to which the present invention relates may be used in any suitable form—whether when alone or when present in a combination with other components or ingredients. The lactic acid bacteria and/or *Bifidobacteria* to which the present invention relates may be referred to herein as "the composition". Likewise, combinations comprising the composition of the present invention and other components and/or ingredients (i.e. ingredients—such as food ingredients, functional food ingredients or pharmaceutical ingredients) may be used in any suitable form.

The lactic acid bacteria and/or *Bifidobacteria* to which the present invention relates may be used in the form of solid or liquid preparations or alternatives thereof. Examples of solid preparations include, but are not limited to tablets, capsules, dusts, granules and powders which may be wettable, spray-dried or freeze-dried. Examples of liquid preparations include, but are not limited to, aqueous, organic or aqueous-organic solutions, suspensions and emulsions.

Suitable examples of forms include one or more of: tablets, pills, capsules, ovules, solutions or suspensions, which may contain flavouring or colouring agents, for immediate-, delayed-, modified-, sustained-, pulsed- or controlled-release applications.

By way of example, if the composition of the present invention is used in a tablet form—such for use as a functional ingredient—the tablets may also contain one or more of: excipients such as microcrystalline cellulose, lactose, sodium citrate, calcium carbonate, dibasic calcium phosphate and glycine; disintegrants such as starch (preferably corn, potato or tapioca starch), sodium starch glycollate, croscarmellose sodium and certain complex silicates; granulation binders such as polyvinylpyrrolidone, hydroxypropylmethylcellulose (HPMC), hydroxypropylcellulose (HPC), sucrose, gelatin and acacia; lubricating agents such as magnesium stearate, stearic acid, glyceryl behenate and talc may be included.

Examples of nutritionally acceptable carriers for use in preparing the forms include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethylcellulose, polyvinylpyrrolidone, and the like.

Preferred excipients for the forms include lactose, starch, a cellulose, milk sugar or high molecular weight polyethylene glycols.

For aqueous suspensions and/or elixirs, the composition of the present invention may be combined with various sweetening or flavouring agents, colouring matter or dyes, with emulsifying and/or suspending agents and with diluents such as water, propylene glycol and glycerin, and combinations thereof.

The forms may also include gelatin capsules; fibre capsules, fibre tablets etc.; or even fibre beverages.

Further examples of form include creams. For some aspects the microorganism used in the present invention may be used in pharmaceutical and/or cosmetic creams such as sun creams and/or after-sun creams for example.

In one aspect, the composition according to the present invention may be administered in an aerosol, for example by way of a nasal spray, for instance for administration to the respiratory tract.

Prebiotics

The composition of the present invention may additionally contain one or more prebiotics. Prebiotics are a category of functional food, defined as non-digestible food ingredients that beneficially affect the host by selectively stimulating the growth and/or activity of one or a limited number of bacteria (particularly, although not exclusively, probiotics, *Bifidobacteria* and/or lactic acid bacteria) in the colon, and thus improve host health. Typically, prebiotics are carbohydrates (such as oligosaccharides), but the definition does not preclude non-carbohydrates. The most prevalent forms of prebiotics are nutritionally classed as soluble fibre. To some extent, many forms of dietary fibre exhibit some level of prebiotic effect.

In one embodiment, a prebiotic is a selectively fermented ingredient that allows specific changes, both in the composition and/or activity in the gastrointestinal microflora that confers benefits upon host well-being and health.

Suitably, the prebiotic may be used according to the present invention in an amount of 0.01 to 100 g/day, preferably 0.1 to 50 g/day, more preferably 0.5 to 20 g/day. In one embodiment, the prebiotic may be used according to the present invention in an amount of 1 to 100 g/day, preferably 2 to 9 g/day, more preferably 3 to 8 g/day. In another embodiment, the prebiotic may be used according to the present invention in an amount of 5 to 50 g/day, preferably 10 to 25 g/day.

Examples of dietary sources of prebiotics include soybeans, inulin sources (such as Jerusalem artichoke, jicama, and chicory root), raw oats, unrefined wheat, unrefined barley and yacon.

Examples of suitable prebiotics include alginate, xanthan, pectin, locust bean gum (LBG), inulin, guar gum, galacto-oligosaccharide (GOS), fructo-oligosaccharide (FOS), polydextrose (i.e. Litesse®), lactitol, lactosucrose, soybean oligosaccharides, isomaltulose (Palatinose™), isomalto-oligosaccharides, gluco-oligosaccharides, xylo-oligosaccharides, manno-oligosaccharides, beta-glucans, cellobiose, raffinose, gentiobiose, melibiose, xylobiose, cyclodextrins, isomaltose, trehalose, stachyose, panose, pullulan, verbascose, galactomannans, and all forms of resistant starches. A particularly preferred example of a prebiotic is polydextrose.

In a yet further aspect, the invention provides use of a combination of:

(a) a lactic acid bacterium, a Bifidobacterium or a mixture of any thereof; and (b) a prebiotic;

in the manufacture of a food product, dietary supplement or medicament for reducing fasted insulin levels in a mammal.

In a yet further aspect, the invention provides use of a combination of:

(a) a lactic acid bacterium, a *Bifidobacterium* or a mixture of any thereof; and (b) a prebiotic;

in the manufacture of a food product, dietary supplement or medicament for increasing insulin secretion at fed state in a mammal.

It is envisaged within the scope of the present invention that the embodiments of the invention can be combined such that combinations of any of the features described herein are included within the scope of the present invention. In particular, it is envisaged within the scope of the present invention that any of the therapeutic effects of the bacteria may be exhibited concomitantly.

EXAMPLES

Example 1

Materials and Methods
Animal Model and Probiotic Treatment

A cohort of fifty C57BI/6 10-wk-old male mice were fed a Normal Chow (NC) (A03, SAFE, Augy, France), or a high-fat diet (HFD) (comprising 72% fat (corn oil and lard), 28% protein and <1% carbohydrates) (SAFE, Augy, France) for 4 weeks. This diet has the peculiar advantage to induce diabetes before the onset of obesity (see for example Cani et al. 2008 "Role of gut microflora in the development of obesity and insulin resistance following high-fat diet feeding". Pathol Biol (Paris); Cani et al, Diabetes, 2008, 57, 1470-81; Knauf et al. *Endocrinology* 2008, 149, 476877; Cani et al., *Diabetologia* 2007, 50, 2374-83; Cani et al. *Diabetes* 2007, 56, 1761-1772 and Turini et al. *Swiss Med Wkly* 2007, 137, 700-4).

Following the high fat diet feeding (before probiotic feeding), the mice underwent an intraperitoneal glucose tolerance test. The area under curve was calculated and the mice dispatched homogeneously according to the different experimental groups or ten mice per group (10 mice per group). The data showed that all mice were in diabetic state before probiotic feeding. The mice were fed four more weeks with a normal chow (n=10) or a HFD (n=40). The HFD mice were treated daily for 4 weeks with one of the following:

1. Vehicle treated
2. *Bifidobacterium animalis* subsp. *lactis* strain 420 (B420) ($10^9$/bacteria per mouse)
3. *Lactobacillus acidophilus* NCFM (NCFM) ($10^9$/bacteria per mouse),
4. NCFM+B420 ($5 \times 10^8$ B420+$5 \times 10^8$ NCFM per mouse).

The mice were housed in a controlled environment (inverted 12-h daylight cycle, light off at 10:00 a.m.).

Endotoxemia and Plasma CD14

Blood samples were collected from the mice in the end of the probiotic or control treatments. Endotoxin assay based on a Limulus amaebocyte extract with Kinetic-QCL test (Bio Whittaker, Cambrex BioScience) was used for the quantification of plasma LPS (endotoxemia)—this is a quantitative, kinetic assay for the detection of Gram-negative bacterial endotoxin. Sera are diluted 1/20 to 1/100 and heated during rounds of 10 min at 70° C. The lower limit of detection of LPS was 0.001 Endotoxin Units/ml. Plasma sCD14, the LPS receptor, was measured using an immuno-enzymatic method (IBL, GmbH, Hamburg, Germany).

Quantification of Microbial DNA in Mouse Tissues

Following sacrifice, the following mouse tissues were harvested aseptically: mesenteric adipose tissue, subcutaneous adipose tissue, and liver. The tissues were snap-frozen and kept frozen until analysis. Prior to DNA extraction, tissues were homogenized using a Precellys 24 automatic biological sample lyser (Bertin Technologies, Tarnos, France). Samples were weighted and diluted with 1.4 ml ASL Buffer (Qiagen, Hilden, Germany) in CK14 tubes containing ceramic beads (Bertin). Samples were milled with beads for 3×30 seconds at 6,800 rpm and kept on ice in between the runs. Supernatant was collected and transferred into VK01 tubes containing glass powder (Bertin) and the milling process was repeated. Supernatant was again collected and transferred into 2 ml Eppendorf tubes. Bacterial DNA was isolated and purified using QIAmp DNA Stool Mini Kit (Qiagen) according to the manufacturer's instructions.

Bacterial DNA was measured by quantitative real-time PCR using group or genus specific primers. The target bacterial groups (and the primers and conditions used) were: total domain *Bacteria* (unpublished), family Enterobacteriaceae (Matsuda et al. *App. Env. Microbiol.*, 2007, 73, 32-39), genus *Bifidobacterium* (Mäkivuokko et al. Nutrition and Cancer 2005, 52(1), 93-103), genus *Lactobacillus* (Walter et al. *Appl. Environ. Microbiol.* 2001, 67, 2578-2585, Heilig et al *Appl. Environ. Microbiol.* 2002, 68, 114-123), class Bacteroidetes and genus *Enterococcus* (Rinttilä et al. *J. Appl. Microbiol.*, 2004, 97, 1166-1177). The equipment used for the quantitative PCR analysis was Applied Biosystems 7500 FAST Real-time PCR System or ABI Prism 7000 Sequence Detection System (Applied Biosystems, Foster City, Calif., USA). The results were expressed as log cells per gram of tissue above the detection limit of each bacterial group in each tissue. The detection limits were determined separately for each bacterial group in each tissue type.

Results
Endotoxemia and Plasma CD14

High fat diet (HFD) was associated with 2-3 times average increase in comparison to the basal endotoxemia (basal level of plasma LPS) of the mice fed with normal chow (NC) (FIG. 1). This increase in plasma LPS associated with high fat diet is defined as metabolic endotoxemia.

All probiotic treatments were able to reduce the metabolic endotoxemia significantly in the mice and reverse the adverse effects of high fat diet. The average level of plasma sCD14, the main receptor of LPS, of mice treated with probiotics and high fat diet was over four times lower than mice who received high fat diet only.

Taken together, the results demonstrate that probiotic treatment reduces metabolic endotoxemia and in addition reduces the circulating receptors of LPS, which are also elevated with high fat diet. LPS is a major cell wall component of gram-negative bacteria, which occurs in the intestine as a component of gram-negative microbiota but also as free LPS. Reduction of metabolic endotoxemia may result from reduction of translocation of gram-negative bacteria into the host, reduction of absorption of free LPS by the host, or enhanced clearance of LPS by the host. Probiotics can therefore be used as an innovative method for preventing of treating metabolic endotoxemia.

Reduction of Bacterial Translocation into Tissues

Figure 2:
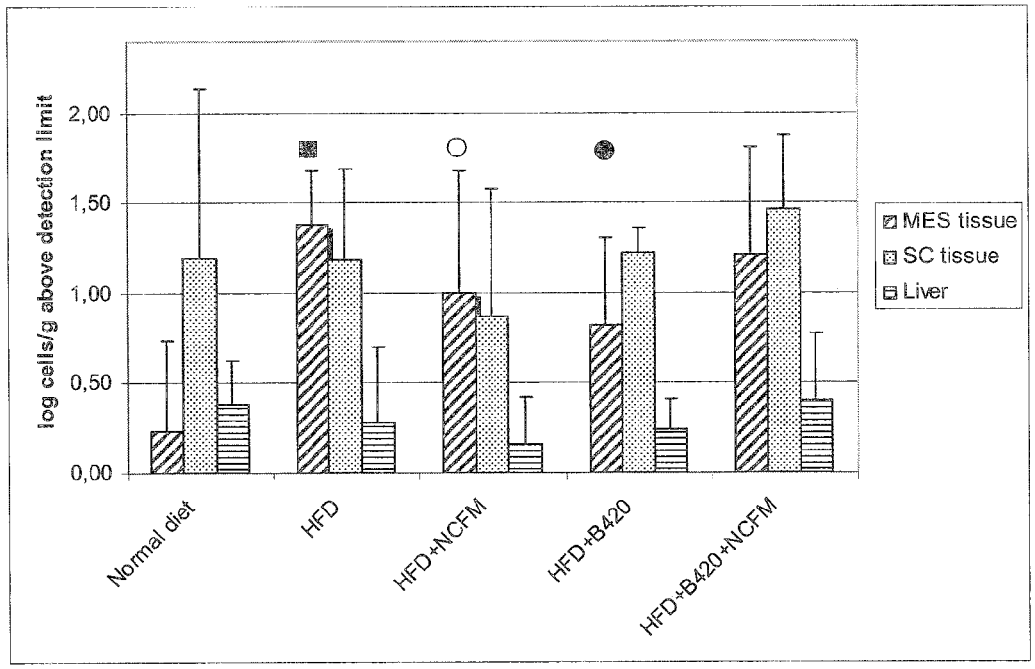
FIG. 2 illustrates the average tissue level of bacteria of the family Enterobacteriaceae (levels above detection limit) in mice administered with normal chow, high fat diet, or high fat diet supplemented with bacteria according to the present invention (NCFM, B420 or NCFM+B420)
Figure 3:
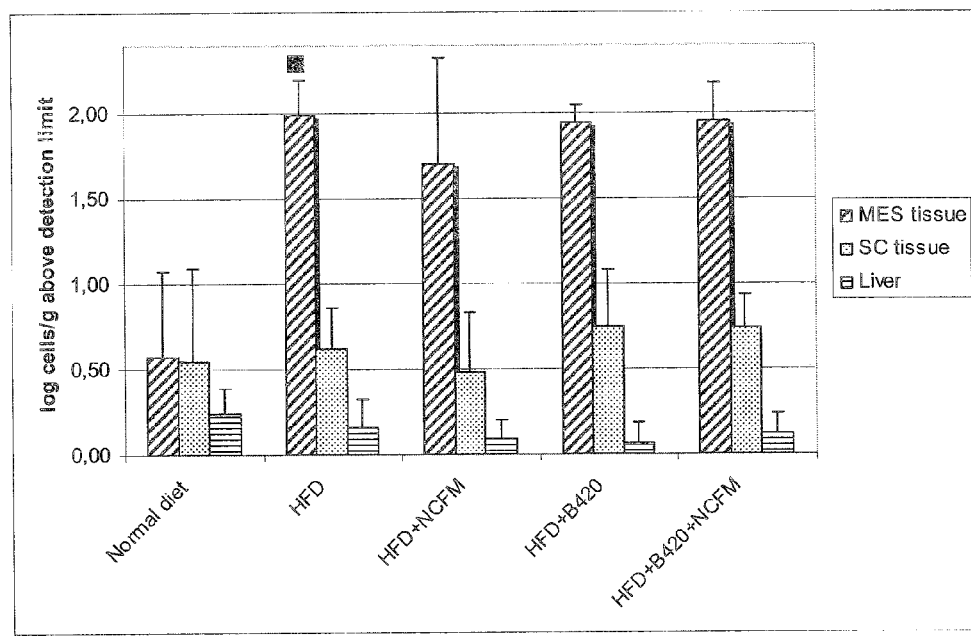
FIG. 3 illustrates the average tissue level of bacteria of the genus *Enterococcus* (levels above detection limit) in mice administered with normal chow, high fat diet, or high fat diet supplemented with bacteria according to the present invention (NCFM, B420 or NCFM+B420)
Figure 4:
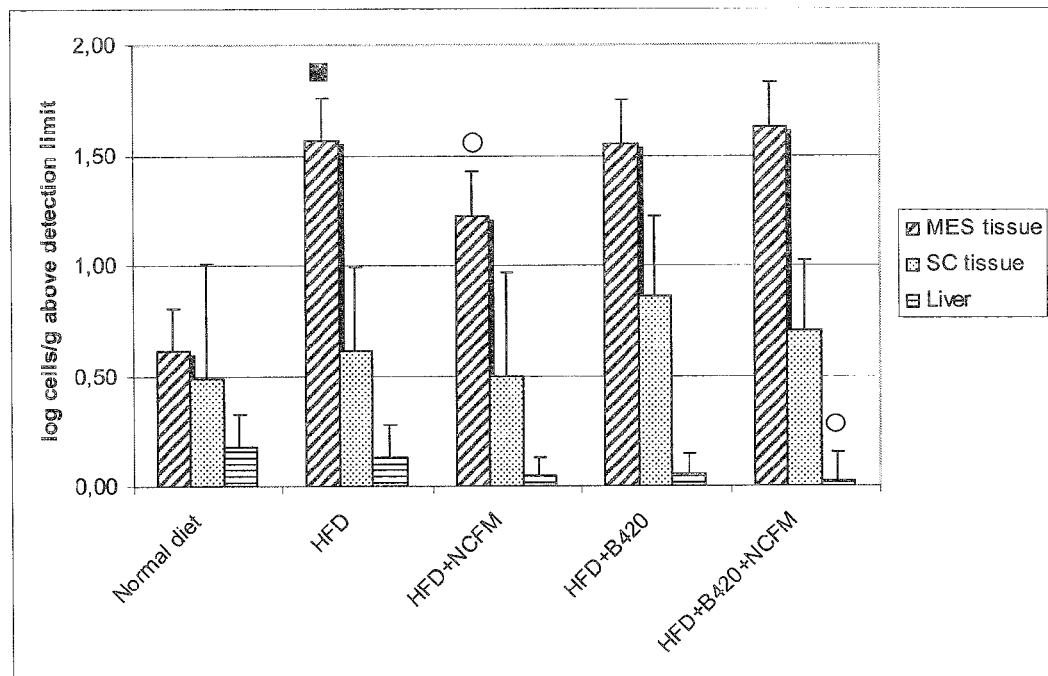
FIG. 4 illustrates the average tissue level of bacteria of the genus *Lactobacillus* (levels above detection limit) in mice administered with normal chow, high fat diet, or high fat diet supplemented with bacteria according to the present invention (NCFM, B420 or NCFM+B420)
Figure 5:
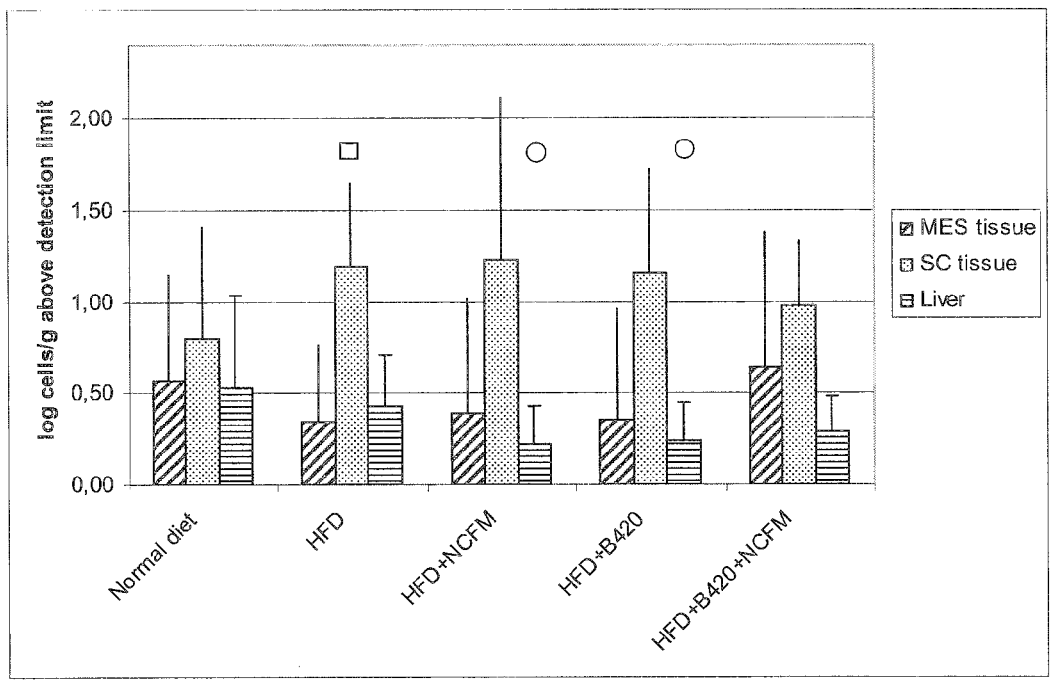
FIG. 5 illustrates the average tissue level of bacteria of the class Bacteroidetes (levels above detection limit) in mice administered with normal chow, high fat diet, or high fat diet supplemented with bacteria according to the present invention (NCFM, B420 or NCFM+B420)
Figure 6:
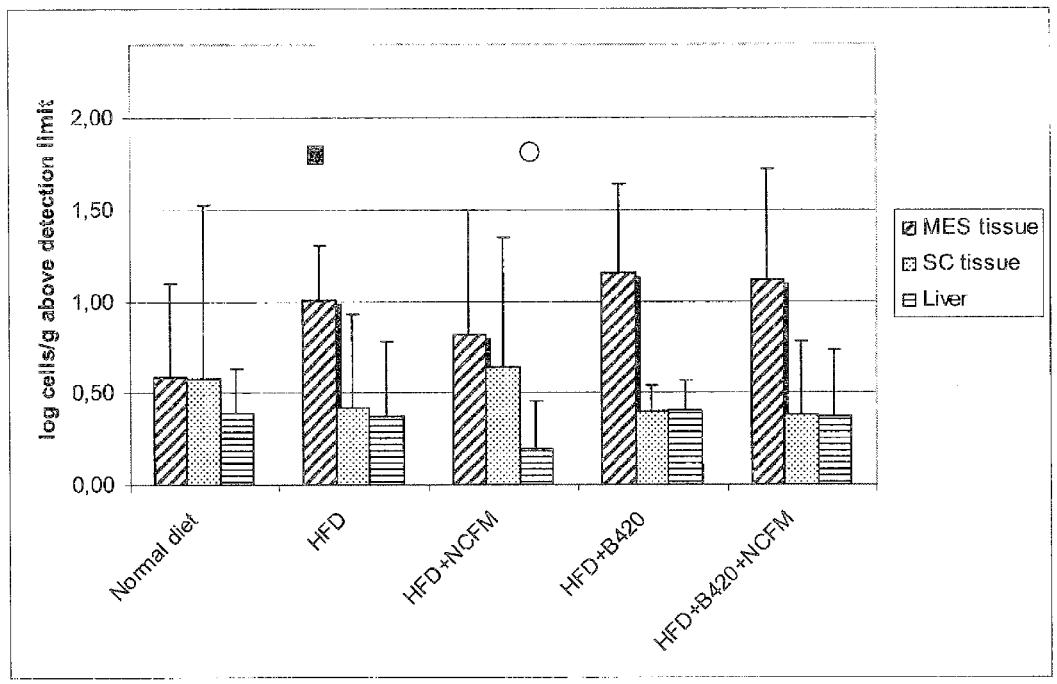
FIG. 6 illustrates the average tissue level of Total Domain Bacterium (levels above detection limit) in mice administered with normal chow, high fat diet, or high fat diet supplemented with bacteria according to the present invention (NCFM, 8420 or NCFM+B420)

High fat diet was associated with elevated levels of bacterial DNA in the tissues, as compared to normal chow. The impact was particularly evident in mesenteric adipose tissue, where elevated levels of the family Enterobacteriaceae (FIG. 2), genus *Enterococcus* (FIG. 3), genus *Lactobacillus* (FIG. 4) and total Domain Bacterium (FIG. 6) were associated with high fat diet. In subcutaneous adipose tissue, elevated levels of class Bacteroidetes were detected in mice fed with high fat diet (FIG. 5). Genus *Bifidobacterium* was not detected in significant amounts in any of the tissues.

Probiotic treatment significantly reduced the levels of bacterial DNA in the tissues. In mesenteric adipose tissue, the B420 treatment significantly reduced the level of family Enterobacteriaceae (FIG. 2), and the NCFM treatment showed a trend for reduced levels of family Enterobacteriaceae (FIG. 2) and genus *Lactobacillus* (FIG. 4). in the liver, the combination of NCFM and B420 tended to reduce the level of genus *Lactobacillus* (FIG. 4), while NCFM treatment alone tended to reduce the levels of class Bacteroidetes (FIG. 5) and the Domain Bacterium (FIG. 6), and the 8420 treatment tended to reduce the levels of class Bacteroidetes (FIG. 5). Statistically non-significant downward trends were also observed for other bacteria and tissues (FIGS. 2 to 6).

The results demonstrate that probiotic treatment can reduce the level of bacteria in metabolically very important tissues, the mesenteric adipose tissue and the liver. Thereby, probiotics may be used as an innovative method for preventing or treating bacterial translocation into tissues, associated with high fat diet and metabolic endotoxemia. Physiologically particularly important may be the reduction of family Enterobacteriaceae in the mesenteric adipose tissue and the class Bacteriodetes in the liver tissue. These two major bacterial groups contain LPS as a component of bacterial cell wall and therefore act as potential source of elevated plasma LPS, which is associated with metabolic endotoxemia. These tissues play particularly important role in metabolic endotoxemia and other metabolic diseases, since LPS causes inflammation in these tissues, potentially leading to a cascade of adverse events including impaired glucose metabolism and reduced insulin sensitivity.

Example 2

Introduction

The aim of this study was to determine in mice the effect of high fat feeding on intestinal flora, bacterial translocation and glycemia, as well as the potential protective role of *Lactobacillus acidophilus* NCFM™ (NCFM™) on these parameters.

Materials and Methods

Obesity and diabetes were induced on C57BL/6 male mice by an high animal fat diet (60% fat, HFD). Control mice received standard diet (4% of fat, LFD). From 19 weeks old, these mice received $10^9$ CFU/day of *Lactobacillus acidophilus* NCFM™ during 3 weeks. Fasting glycemia was measured before and after treatment with NCFM™.

An intraperitoneal insulin sensitivity test was performed the day before the sacrifice. Analysis of colonic adherent flora and bacterial translocation was done by the following methods.

Bacterial Analysis

After dissection colon and ileum were harvested. Ileal and colon wall was used to identify and quantify the adherent flora.

Samples were conserved up to 2 hours in Ringer/Tween 80 medium under anaerobic conditions. After homogenisation, samples were incubated in Brain Heart Broth to enrich and identify the highest number of anaerobes and aero-anaerobes bacteria.

1 in 10 and 1 in 100 dilutions were performed in Ringer cysteine medium. These dilutions were spread out on Columbia agar enriched with 5% defibrinated horse blood (CS) and incubated at 37° C. under aerobe or anaerobe atmosphere. Colonies were counted and identified 2 and 7 days after spreading.

Three types of medium were used. Some unselective agar, CL agar (Deoxycholate, Citrate, and Lactose) to isolate enterobacteria and MRS agar (Man, Rogosa, Sharpe) specific for *Lactobacillus* spp. Identification of the bacteria was performed by the determination of the respiratory type, the Gram staining and the metabolic features.

Bacterial Translocation

After dissection, mesenteric lymph nodes (MLN) and mesenteric adipose tissue (MAT) were harvested. Bacterial translocation was quantified in MLN and MAT.

Samples were conserved up to 2 hours in Ringer/Tween 80 medium under anaerobic conditions. After homogenisation, 1 mL of the initial samples was inoculated in brain-heart enrichment broth in order to diminish the detection threshold for samples with a low bacterial level. Enrichment cultures were covered by a layer of paraffin in order to allow growth of anaerobes incubated for four days and checked for growth daily.

Positive cultures were isolated on modified Columbia blood agar plates incubated 48 h under anaerobic conditions. Different types of colonies were subcultured and identified. All incubations were done at 37° C. Bacterial counts were established and expressed as log CFU/g of tissue.

Results

At 18 weeks old, high fat diet mice (HFD) weighed 39% ore than control diet mice (LFD) (39.2±3.3 vs 28.1±1.1 g, p<0.01). Fasting hyperglycemia increased by 77% (174±31 vs 98±6 mg/dl, p<0.01), and insulin sensitivity decreased (2 vs 48% of glycemia decrease 60 min after insulin injection) were found in HFD group compared with LFD.

*Lactobacillus acidophilus* NCFM™ administration did not modify fasting glycemia of LFD mice (95±5 mg/dl vs. 92±6 mg/dl). However, glycemia of HFD mice was significantly decreased, which trended to normalization (226±23 mg/dl vs 125±10 mg/dl, p<0.02). HFD mice treated with NCFM™ remained resistant to insulin.

HFD mice showed colonic adherent flora significantly more abundant (6.5±0.7 vs 4.6±0.4 logCFU/g, p<0.01) including more *Lactobacilli* (6.0±0.5 vs 4.5±0.2, p<0.01) and *Enterococci* (5.4±0.4 vs 4.4±0.2 logCFU/g, p<0.01). This excess was canceled by NCFM™ treatment (back to 5.4±0.6 logCFU/g for total flora, 4.3±0.2 logCFU/g for *Lactobacilli*, and 4.6±0.4 logCFU/g for *Enterococci*). The increase of bacteria detected in mesenteric fat of HFD mice (3.8±1.5 vs 2.2±0.9 logCFU/g) was slightly modified by NCFM™ treatment (4.0±1.2 logCFU/g). In colon and ileum of HFD mice, flora diversified with appearance of Gram-negative bacteria, which were not cleared by NCFM™. In mesenteric lymph nodes, Gram-positive bacteria appeared on high fat diet mice, and disappeared after NCFM™ treatment.

Conclusion

Probiotic strain *Lactobacillus acidophilus* NCFM™ tended to normalize fasting hyperglycemia of obese and diabetic mice. The latter showed adherent intestinal flora more abundant and more diversified than control mice. Treatment with *Lactobacillus acidophilus* NCFM™ led to decrease of mucosa-adhered bacteria levels in the colon, and to clearance of potentially pathogenic Gram-positive bacteria in ileum, colon and mesenteric lymph nodes.

Example 3

Measurement of Mucosa-adherent and Luminal *Escherichia coli* and *E. coli* Translocation Effect of probiotic treatment on mucosal adhesion and bacterial translocation of *E. coli* was determined by culturing. The mouse model and the probiotic treatment used were the same as described in Example 1 above. In addition, a group receiving a combination of the probiotic with a prebiotic component (fructo-oligosaccharides at 0.2 g per animal per day) was included.

Fasted mice were gavaged with $10^9$ colony forming units of ampicillin resistant *E. coli* isolated from the mouse and rendered ampicillin resistant by the mean of a plasmid expressing the β-lactamase gene under the control of a prokaryotic promoter. Two hours later the mice were sacrificed and the mucosa or the lumen from the duodenum, the jejunum, the ileum, the caecum and the colon, were harvested separately, diluted, plated onto ampicillin-containing agarose and incubated overnight at 37° C. The number of colonies was counted. Similarly, ampicillin resistant fluorescent *E. coli* was cultured from harvested tissues including liver, spleen, mesenteric adipose tissue, subcutaneous adipose tissue, mesenteric ganglion and subcutaneous ganglion. Insulin concentration was measured from plasma in fasted state as well as in fed state.

Results

Figure 7:
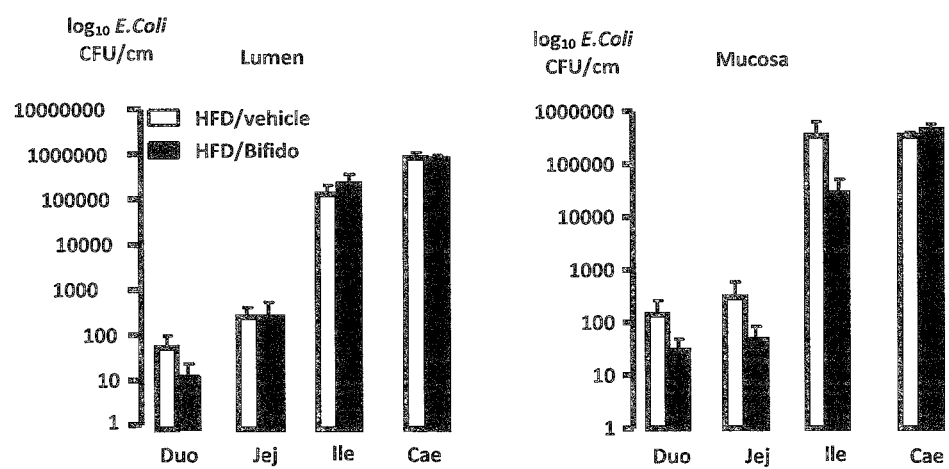
FIG. 7 illustrates the levels of *E. coli* in the mucosa or different segments of the lumen of mice administered a high fat diet and treated with vehicle or a high fat diet supplemented with bacteria according to the present invention (B420)
Figure 8:
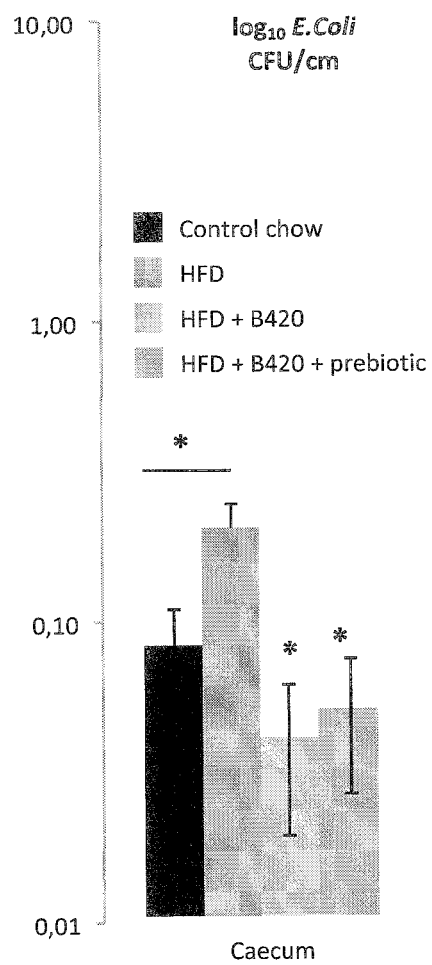
FIG. 8 illustrates the effect on the adhesion of *Escherichia coli* in the mucosa of the caecum of mice administered a high fat diet and treated with vehicle or a high fat diet supplemented with bacteria according to the present invention (B420), alone or in combination with a prebiotic.

In order to investigate the role of mucosal adhesion in this process, the adherence of antibiotic-resistant commensal *Escherichia coli* into the mouse intestinal mucus was quantified. The quantification of antibiotic resistant colonies on an agarose plate originating from the mucosa or different segments of the lumen showed that the HFD diet elevated the levels of mucosa-associated *E. coli*, but treatment with probiotic strain B420 reduced the HFD-induced *E. coli* mucosal adherence to the jejunum and the ileum (FIG. 7). Although initial tests revealed no changes in the caecum or colon, further tests showed that probiotic strain 420 reduced the HFD-induced *E. coli* mucosal adherence to the caecum (FIG. 8).

Figure 9:
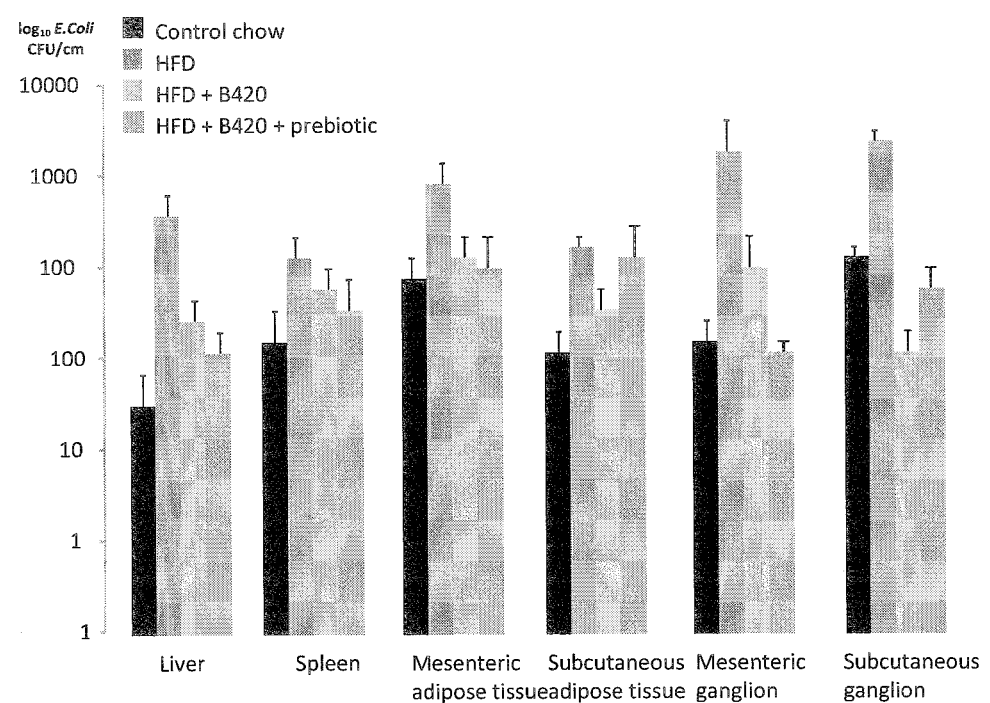
FIG. 9 illustrates the effect on the translocation of *Escherichia coli* into the host tissues of mice administered a high fat diet and treated with vehicle or a high fat diet supplemented with bacteria according to the present invention (B420), alone or in combination with a prebiotic.
Figure 10:
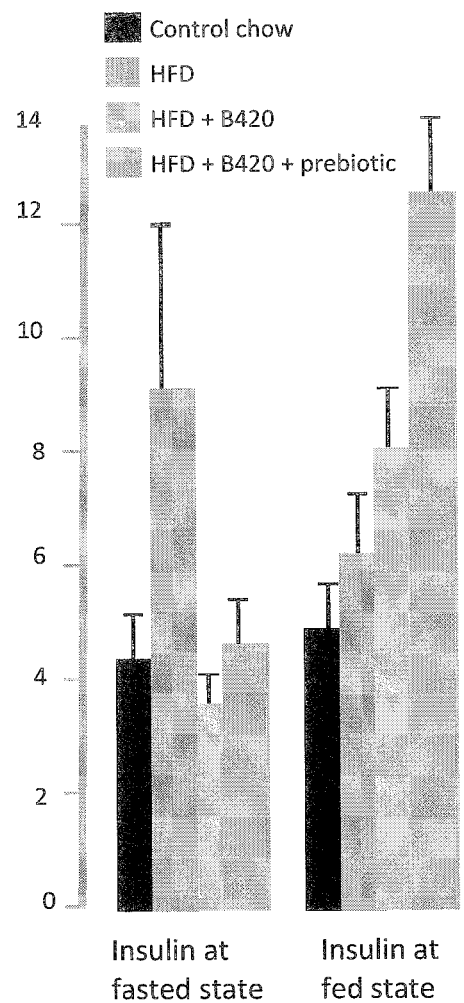
FIG. 10 illustrates the effect on fasted insulin levels and insulin secretion at fed state of mice administered a high fat diet and treated with vehicle or a high fat diet supplemented with bacteria according to the present invention (B420), alone or in combination with a prebiotic.

Treatment with B420 alone or in combination with a prebiotic also reduced the translocation of *E. coli* into mouse tissues including tissues including liver, spleen, mesenteric adipose tissue, subcutaneous adipose tissue, mesenteric ganglion and subcutaneous ganglion (FIG. 9). Reduction of mucosal adhesion and translocation of *E. coli* was accompanied with improved insulin levels, namely, reduced fed insulin levels and improved insulin secretion upon feeding (FIG. 10).

Example 4

Reduction of Gene Expression

Materials & Methods

Caco-2 cells (ECACC, Salisbury, UK) were used as a model for human intestinal epithelial cells (IECs) as in Putaala H, et al. ("Effect of four probiotic strains and *Escherichia coli* O157:H7 on tight junction integrity and cyclo-oxygenase expression", *Research in Microbiology* 2008) and Makivuokko H, et al. (*Nutr. Cancer,* 2005, 52, 94-104). in standard in vitro culture conditions comprising a humified athmosphere at 37° C. with 5% $CO_2$, and Caco-2 cell culture media (Invitrogen, Carlsbad, Calif., US and BD Biosciences, San Jose, Calif., US).

For exposure of Caco-2 cells *Bifidobacterium animalis* ssp. *lactis* 420 was propagated in Man, Rogosa and Sharpe (MRS) broth overnight, bacterial cell densities determined with flow cytometry (FACS Calibur, Becton Dickinson, San Jose, Calif., US), pelleted (25° C., 5 min, 3000 g), washed once with Caco-2 culture medium, and diluted into Caco-2 culture medium in a ratio of 20 to 100 bacterial cells to one Caco-2 cell. After this the Caco-2 cells were treated for 8 hours in standard in vitro conditions. As a control, Caco-2 cells treated with Caco-2 culture medium without added *B. animalis* ssp. *lactis* 420 were used.

For exposure of Caco-2 cells with polydextrose, 1% (v/v) and 2% (v/v) polydextrose (Litesse®) in colon simulation medium were first fermented in an in vitro colon simulator as in Makivuokko et al. referred to above. The in vitro colon simulation consisting of four stages and of four parallel units was used in this study.

A single unit comprises four sequentially connected vessels (V1, V2, V3 and V4) with conditions adjusted to represent different parts of the human colon in series representing different parts of colon: proximal, ascending, descending, and distal colon. After simulation the polydextrose fermentation supernatants were pelleted (25° C., 5 min, 10,000 g), diluted 10% (v/v) into Caco-2 culture medium. The cells were treated for 24 h in standard in vitro conditions. As a control, Caco-2 cells treated similarly with fermented colon simulation medium without added polydextrose were used.

After exposure, total cellular RNA was isolated from Caco-2 cells using RNeasy mini kit (Qiagen, Hilden, Germany). Affymetrix U133+2.0 GeneChips (Affymetrix Inc. Santa Clara, Calif., US) were used to study the human cell transcriptome. All RNA processing, labelling, hybridizations, washing, staining and scanning during the microarray processing were performed according to the manufacturer's standard recommendations.

Microarray data was pre-processed with GC-RMA, and analyzed statistically using programming language R (version 2.5.0) (R Development Core Team; "R:A language and environment for statistical computing", Vienna, Austria: R Foundation for Statistical Computing; 2006), and Bioconductor (version 2.0) (Gentleman R C et al. "Bioconductor: open software development for computational biology and bioinformatics" *Genome Biol.* 2004, 5, R80). Differentially expressed genes were selected based on gene expression with more than 1.6 log-ratio difference in the signal intensity compared with that of control for samples treated with *B. animalis* ssp. *lactis* 420. For polydextrose treated Caco-2 samples differentially expressed genes were selected based on their total behaviour calculated using the norm of genes from the three last vessels (V2, V3, V4) of simulation.

Most of the genes followed similar pattern across the four vessels: within down-regulated or up-regulated profiles the expression decreased or increased towards the last vessel. Also, if a gene profile was up-regulated in control, 0% polydextrose, it was slightly more up-regulated in 1% polydextrose treatment and even more in 2% polydextrose. Similarly, in down-regulated profiles, the 2% polydextrose treatment was more down-regulated than 1% which was more down-regulated than control. Thereby, genes were defined as either up- or down-regulated based on the last three vessels. The difference between the non-treated samples and two polydextrose concentrations was calculated using Student's t-test for paired samples with cut-off p-value p<0.01.

Results

Expression of intestinal cholesterol absorption-related genes is regulated in Caco-2 cells by *B. animalis* ssp. *lactis* 420 (Table 1) or by polydextrose fermentation supernatants (Table 2).

The downregulative effect on APOB, APOC2, APOC3, APOAIV and MTTP have reductive effect on cholesterol and triglyceride absorption from the intestine (Iqbal J and Hussain M M, *American Journal of Physiology-Endocrinology and Metabolism* 2009, 296, E1183-E1194), whereas upregulative effect on NPC1 increases the formation of HDL in the intestine (Branham L R et al, *J Clin Invest* 2006, 116, 1052-62). NR2F2 and HNF4A are transcription factors that regulate the expression of apolipoprotein genes: see Antes T J, et al. *Biochemistry* 2101, 40, 6720-30 and Leng S Y, et al. *American Journal of Physiology-Gastrointestinal and Liver Physiology*, 2007, 293, G475-G483.

TABLE 1

Effect of *Bifidobacterium animalis* ssp. *lactis* 420

| Gene | Expression level |
|---|---|
| Apolipoprotein B (APOB) | −2.89 |
| Apolipoprotein C-II (APOC2) | −2.53 |
| Apolipoprotein C-III (APOC3) | −1.47 |
| Apolipoprotein A-IV (APOAIV) | −2.84 |
| Microsomal triglyceride transfer protein (MTTP) | −2.99 |
| Nuclear receptor subfamily 2, group F, member 2 (NR2F2), also known as ARP1 | −1.67 |
| Hepatocyte nuclear factor 4, alpha (HNF4A) | −2.3 |

TABLE 2

Effect of polydextrose fermentation

| | Expression level | | | | | | | |
|---|---|---|---|---|---|---|---|---|
| | 1% V1 | 1% V2 | 1% V3 | 1% V4 | 2% V1 | 2% V2 | 2% V3 | 2% V4 |
| Niemann-Pick disease, type C1 (NPC1) | 1.03 | 1.87 | 1.62 | 1.68 | 1.20 | 1.82 | 1.99 | 1.78 |

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. indeed, various modifications of the described modes for carrying out the invention which are obvious to those skilled in biochemistry and biotechnology or related fields are intended to be within the scope of the following claims.

The invention claimed is:

1. A method of treating metabolic endotoxemia in a mammal in need thereof, the method comprising administering an effective amount of a bacterium selected from a lactic acid bacterium, a *Bifidobacterium* or a mixture of any thereof, wherein the metabolic endotoxemia is induced by a high fat diet.

2. A method according to claim 1, wherein the endotoxemia comprises an increase of the level of lipopolysaccharides in the mammal by a factor in the range from 2 to 4 compared with basal lipopolysaccharide levels.

3. A method according to claim 1, wherein the bacterium is a probiotic lactic acid bacterium and/or a probiotic *Bifidobacterium*.

4. A method according to any claim 1, wherein the bacterium is a bacterium selected from the genera *Lactobacillus* or *Bifidobacterium* and mixtures thereof.

5. A method according to claim 4, wherein the bacterium is selected from the species *Lactobacillus acidophilus*, *Lactobacillus plantarum*, *Bifidobacterium animalis*, *Bifidobacterium lactis*, or *Bifidobacterium bifidium*, and mixtures thereof.

6. A method according to claim 5, wherein the bacterium is *Lactobacillus acidophilus* strain NCFM, *Bifidobacterium animalis* subsp. lactis strain 420, *Lactobacillus salivarius* strain 33, or a mixture thereof.

7. A method according to claim 1, wherein the mammal is diabetic and obese.

8. A method according to claim 1, wherein the mammal is diabetic and non-obese.

9. A method according to claim 1, wherein the mammal is non-diabetic and obese.

10. A method according to claim 1, wherein the mammal continues to ingest a high-fat diet during the course of the treatment.

11. A method according to claim 1, wherein the bacterium is administered in combination with one or more prebiotics.

12. A method according to claim 11, wherein the prebiotic is selected from alginate, xanthan, pectin, locust bean gum, inulin, guar gum, a galacto-oligosaccharide, a fructo-oligosaccharide, polydextrose, lactitol, lactosucrose, a soybean oligosaccharide, palatinose, an isomalto-oligosaccharide, a gluco-oligosaccharide or a xylo-oligosaccharide, or a mixture of any thereof.

13. A method according to claim 12, wherein the prebiotic is polydextrose.

14. A method according to claim 1, wherein the endotoxemia comprises an increase of the level of lipopolysaccharides in the mammal by a factor in the range from 1.5 to 20 compared with basal lipopolysaccharide levels.

\* \* \* \* \*

UNITED STATES PATENT AND TRADEMARK OFFICE
CERTIFICATE OF CORRECTION

PATENT NO. : 9,259,447 B2
APPLICATION NO. : 13/384748
DATED : February 16, 2016
INVENTOR(S) : Rémy Burcelin et al.

It is certified that error appears in the above-identified patent and that said Letters Patent is hereby corrected as shown below:

In the claims

Column 24, Line 56, Delete "any" before "claim"

Signed and Sealed this
Tenth Day of May, 2016

Michelle K. Lee
*Director of the United States Patent and Trademark Office*